United States Patent
Leppala et al.

(10) Patent No.: US 10,395,770 B2
(45) Date of Patent: Aug. 27, 2019

(54) SYSTEMS AND METHODS FOR MONITORING A PATIENT

(71) Applicant: General Electric Company, Schenectady, NY (US)

(72) Inventors: Kristina Maria Leppala, Vantaa (FI); Milvi Kristiina Soosalu, Espoo (FI); Virpi Kristiina Lahdenmaki, Helsinki (FI)

(73) Assignee: General Electric Company, Schenectady, NY (US)

( * ) Notice: Subject to any disclaimer, the term of this patent is extended or adjusted under 35 U.S.C. 154(b) by 144 days.

(21) Appl. No.: 15/434,464

(22) Filed: Feb. 16, 2017

(65) Prior Publication Data

US 2018/0232494 A1    Aug. 16, 2018

(51) Int. Cl.
*G06F 3/048* (2013.01)
*G16H 40/63* (2018.01)
*G06F 3/0484* (2013.01)
*H04L 29/06* (2006.01)

(52) U.S. Cl.
CPC ......... *G16H 40/63* (2018.01); *G06F 3/04845* (2013.01); *G06F 3/04847* (2013.01); *H04L 67/42* (2013.01)

(58) Field of Classification Search
CPC ... G06F 19/00; G06F 19/3418; A61B 5/7271; A61B 5/743; A61B 5/742; A61B 5/746; A61B 5/0002; A61B 5/002; A61B 5/7445; G06Q 50/24; G16H 10/60; G16H 40/20
See application file for complete search history.

(56) References Cited

U.S. PATENT DOCUMENTS 4,631,214 A * 12/1986 Hasegawa ................ G21F 1/10
                                                174/388
5,590,660 A * 1/1997 MacAulay ............. A61B 1/043
                                                600/160
7,774,052 B2   8/2010 Burton et al.
(Continued)

OTHER PUBLICATIONS

Sangachand et al.; Continuous ST-segment monitoring: nurses' attitudes, practices and quality of patient care; Decision Support, Evidence Series; 2013 (2 pages).
(Continued)

*Primary Examiner* — Linh K Pham
(74) *Attorney, Agent, or Firm* — Dean D. Small; The Small Patent Law Group, LLC

(57) ABSTRACT

System is configured to present a health-monitoring window in an operator display. The health-monitoring window includes a set of graph regions. Each of the graph regions of the set has a background and a signal line of a patient parameter. For at least one of the graph regions of the set, the processor is also configured to determine that the patient parameter for a designated time is significant based upon a predetermined standard. The processor is also configured to provide a reference color to the background for the designated time. The reference color includes at least one of a plurality of potential reference colors. The background for the designated time has a fixed position with respect to the parameter signal line such that an area of the background having the reference color appears to move along the horizontal axis with the parameter signal line as time progresses.

20 Claims, 13 Drawing Sheets

(56) References Cited

U.S. PATENT DOCUMENTS

| | | | |
|---|---|---|---|
| 7,881,778 B2 | 2/2011 | Rantala | |
| 7,925,337 B2 | 4/2011 | Rajagopalan et al. | |
| 8,515,531 B2 | 8/2013 | Costa Ribalta et al. | |
| 8,583,222 B2 | 11/2013 | Nelwan et al. | |
| 9,053,583 B1* | 6/2015 | Gross | G06F 19/3418 |
| 2002/0147383 A1* | 10/2002 | Weber | A61B 1/043 |
| | | | 600/109 |
| 2005/0182333 A1 | 8/2005 | Nagata et al. | |
| 2007/0211274 A1* | 9/2007 | Donomae | H04N 1/60 |
| | | | 358/1.9 |
| 2009/0089100 A1* | 4/2009 | Nenov | G06Q 50/22 |
| | | | 705/3 |
| 2010/0004710 A1* | 1/2010 | Kellum | A61B 5/0002 |
| | | | 607/5 |
| 2010/0317931 A1* | 12/2010 | Sarkela | G16H 15/00 |
| | | | 600/301 |
| 2011/0184692 A1 | 7/2011 | Andersen | |
| 2011/0230731 A1* | 9/2011 | Rantala | G16H 50/30 |
| | | | 600/301 |
| 2012/0053422 A1* | 3/2012 | Rantala | A61B 5/02055 |
| | | | 600/300 |
| 2012/0198341 A1* | 8/2012 | Pekarske | G06F 3/0481 |
| | | | 715/733 |
| 2012/0319848 A1* | 12/2012 | Coffeng | A61B 5/746 |
| | | | 340/573.1 |
| 2012/0323133 A1 | 12/2012 | Lindauer et al. | |
| 2012/0330112 A1* | 12/2012 | Lamego | G06F 19/00 |
| | | | 600/301 |
| 2013/0045685 A1* | 2/2013 | Kiani | G08B 21/24 |
| | | | 455/41.2 |
| 2013/0162433 A1* | 6/2013 | Muhsin | G06F 17/30516 |
| | | | 340/573.1 |
| 2013/0246089 A1* | 9/2013 | Gross | G16H 40/63 |
| | | | 705/2 |
| 2015/0011902 A1 | 1/2015 | Wang | |
| 2015/0051462 A1 | 2/2015 | Olsen | |
| 2015/0097701 A1* | 4/2015 | Al-Ali | A61B 5/0002 |
| | | | 340/870.07 |
| 2017/0308662 A1* | 10/2017 | Hamilton | A61B 5/4362 |

OTHER PUBLICATIONS

Using ST Map to shorten response time and improve efficiency; Decision Support, Evidence Series; 2010 (2 pages).

Martin et al.; An Interactive Tool for the Evaluation of ECG Visualisation Formats; Computing in Cardiology 2013; 40: 779-782.

Steg et al.; ESC Guidelines for the management of acute myocardial infarction in patients presenting with ST-segment elevation; European Heart Journal; Sep. 11, 2012; 51 pages.

Sandau et al.;Continuous ST-Segment Monitoring: Protocol for Practice; American Association of Critical-Care Nurses; vol. 29, No. 4; Aug. 2009; pp. 39-51.

Drew et al.; Practice Standards for Electrocardiographic Monitoring in Hospital Settings; American Heart Association, Inc. Oct. 26, 2004; 30 pages.

Bruhn et al.; Depth of Anaesthesia monitoring: what's available, what's validated and what's next?; British Journal of Anaesthesia 97 (1): 2006; pp. 85-94.

Bond et al.; A usability evaluation of medical software at an expert conference setting; Computer Methods and Programs in Biomedicine 113, 2014; pp. 383-395.

Sangkachand et al.; Continuous ST-Segment Monitoring: Nurses' Attitudes, Practices, and Quality of Patient Care; American Journal of Critical Care; May 2011; vol. 20, No. 3; 14 pages.

Musizza et al.; Monitoring the Depth of Anaesthesia; Sensors, 2010, 10 pp. 10896-10935.

Masimo Corporation; Halo: Assessing Global Patient Status with the Halo Index; 2011; 8 pages.

* cited by examiner

SYSTEMS AND METHODS FOR MONITORING A PATIENT

BACKGROUND

The subject matter herein relates generally to patient monitoring systems and methods, and more particularly, to patient monitoring systems and methods that monitor multiple parameters to facilitate identifying alarm conditions.

Patient monitoring systems are configured to receive physiological data from a patient, analyze the physiological data, and communicate information to a healthcare provider so that the healthcare provider may assess a condition of the patient. Monitoring systems may include one or more detection devices that detect the physiological data and an operator display that presents the information to the healthcare provider. The information includes recognizable physiological parameters that the healthcare provider may use to determine a health status or condition of the patient. Non-limiting examples of these parameters include heart rate, blood pressure, electrocardiographic (ECG) data, auditory evoked potentials, and electroencephalogram (EEG) data. ECG data, in particular, may be used to diagnose certain cardiac conditions, such as complex arrhythmias, myocardial ischemia, and prolonged QT intervals. EEG data may be used to assess a patient's depth of sedation (or depth of anesthesia). A set of patient parameters may also be used to determine a patient's health index, which may represent a physiological deterioration of the patient. Diagnosing the above conditions often includes simultaneously analyzing multiple parameters. This diagnosis is made more difficult because the values that may be considered problematic depend upon the patient.

Monitoring systems are often particularly configured for monitoring certain conditions. For example, monitoring systems may exist for detecting ECG data and analyzing the ST-segments from the ECG data. Changes in ST-segments may indicate myocardial ischemia in which blood flow to the patient's heart is reduced. Traditional ST-segment monitoring systems present a table to the healthcare provider. For example, the healthcare provider may be presented with a table having eleven values that can be positive or negative and are updated in real-time. The tables may compare only one heart beat versus another heart beat. In some cases, the healthcare provider must be specially trained for a particular monitoring system in order to be able to identify when a significant event occurred. Although these ST-segment monitoring systems provide useful information for assessing a patient's health, it is often difficult to interpret the information quickly. Because they can be difficult or frustrating to use, some healthcare providers decide not to use the systems.

Another, more recent, ST-segment monitoring system displays two multi-axis portraits or maps of the ST-segment data. In each portrait, six axes intersect one another at a center of the portrait and each axis intersects a perimeter of the portrait. The ends of the axes, which are positioned along the perimeter of the portrait, correspond to the placement of the electrodes used to obtain the ECG data from the patient. While monitoring a patient, colored sections are shown on the portrait that indicate areas of the heart that are indicating ischemia. Again, although this ST-segment monitoring system provides useful information for assessing a patient's status, the portraits are not intuitive and it is often difficult to interpret the information quickly and/or correctly. A substantial amount of education may be necessary so that the healthcare provider will feel comfortable using the system. Such portraits may also not provide a historical record that shows the user how the patient's health status has changed over a designated time period.

BRIEF DESCRIPTION

In an embodiment, a system is provided that includes an operator display and a processor and a storage medium. The storage medium is configured to store programmed instructions accessible by the processor, wherein, responsive to execution of the programmed instructions, the processor is configured to present (e.g., show or display) a health-monitoring window in the operator display. The health-monitoring window is based on physiological data of a patient and includes a set of graph regions. Each of the graph regions of the set has a background and a signal line of a patient parameter appearing over the background. The signal line is plotted with respect to horizontal and vertical axes of the health-monitoring window. The horizontal axis represents time and the vertical axis represents the patient parameter of the signal line that is based on the physiological data. For at least one of the graph regions of the set, the processor is also configured to determine that the patient parameter for a designated time is significant based upon a predetermined standard. The processor is also configured to provide, in response to determining that the patient parameter is significant for the designated time, a reference color to the background for the designated time. The reference color includes at least one of a plurality of potential reference colors. The background for the designated time has a fixed position with respect to the parameter signal line such that an area of the background having the reference color appears to move along the horizontal axis with the parameter signal line as time progresses.

In one or more aspects, the processor is configured to display multiple separate areas of the background in which the separate areas correspond to respective time periods in which the patient parameter was significant. The separate areas have at least one of the plurality of potential colors.

In one or more aspects, the background has a background color for time periods in which the patient parameter is not significant. The background color is distinct with respect to the potential reference colors.

In one or more aspects, the reference color is selected from the potential reference colors based on whether the patient parameter is above an upper limit or below a lower limit. The reference color for the patient parameter above the upper limit and the reference color for the patient parameter below the lower limit have respective wavelengths. The wavelengths are separated by at least 30 nanometers (nm).

In one or more aspects, the processor is configured to determine that the patient parameter of the corresponding graph region is significant for at least a plurality of the graph regions. For each of the graph regions of the plurality, the processor assigns a corresponding reference color to the background for a designated time in response to determining that the patient parameter is significant for the designated time. The reference color includes at least one of a plurality of potential reference colors. The background for the designated time has a fixed position with respect to the parameter signal line such that an area of the background having the reference color moves along the horizontal axis with the parameter signal line as time progresses.

Optionally, at least some of the graph regions of the plurality of the graph regions are vertically stacked and the parameter signal lines of the graph regions that are vertically stacked are essentially synchronized. The health-monitoring window includes a time indicator that extends generally parallel to the vertical axis of the health-monitoring window and across the graph regions that are vertically stacked. The time indicator is movable along the horizontal axis of the health-monitoring window. The processor is configured to receive user inputs for positioning the time indicator along the horizontal axis.

In one or more aspects, the health-monitoring window is configured to include a color legend. The color legend includes the potential reference colors for viewing by a user of the system. The color legend also includes a scale that associates values of the patient parameter with the potential reference colors.

In one or more aspects, the patient parameters correspond to electrocardiographic (ECG) data. In one or more aspects, the system is an ST-segment monitoring system.

In one or more aspects, the reference color is selected from the potential reference colors based on how much the patient parameter is significant. Optionally, the reference color is selected from the potential reference colors based on whether the patient parameter is above an upper limit or below a lower limit. The reference color above the upper limit and the reference color below the lower limit being selected from separate color spectrums, the color spectrums being separated by at least 30 nanometers (nm).

In one or more aspects, only a portion of the background for the designated time has the reference color. The reference color exists between the parameter signal line and a horizontal line of the graph region. The parameter signal line being a border of the background that has the reference color.

In one or more aspects, the reference color extends between a top horizontal line positioned above the parameter signal line and a bottom horizontal line positioned below the parameter signal line. The parameter signal line is visible over the background that has the reference color.

In an embodiment, a method (e.g., a method for monitoring a condition of a patient) is provided. The method includes receiving physiological data from a patient and presenting a health-monitoring window in an operator display. The health-monitoring window includes a set of graph regions. Each of the graph regions of the set has a background and a parameter signal line appearing over the background. The parameter signal line is plotted with respect to horizontal and vertical axes of the health-monitoring window. The horizontal axis represents time and the vertical axis represents a patient parameter that is based on the physiological data. For at least some of the graph regions, the method also includes determining that the patient parameter of a corresponding graph region is significant for a designated time and providing a reference color to the background of the corresponding graph region for the designated time. The reference color includes at least one of a plurality of potential reference colors. The background for the designated time has a fixed position with respect to the parameter signal line such that an area of the background having the reference color moves along the horizontal axis with the parameter signal line as time progresses.

In one or more aspects, the background is configured to include multiple separate areas in which the separate areas correspond to respective time periods in which the patient parameter was significant. The separate areas have at least one of the plurality of potential colors.

In one or more aspects, the reference color is selected from the potential reference colors based on whether the patient parameter is above an upper limit or below a lower limit. The reference color for the patient parameter above the upper limit and the reference color for the patient parameter below the lower limit have respective wavelengths. The wavelengths are separated by at least 30 nanometers (nm), wherein the background has a background color for time periods in which the patient parameter is not significant. The background color is distinct with respect to the potential reference colors. Optionally, the method includes receiving user inputs for selecting at least one of the upper limit or the lower limit.

In one or more aspects, at least some of the graph regions of the plurality of the graph regions are vertically stacked and the parameter signal lines of the graph regions that are vertically stacked are essentially synchronized. The health-monitoring window includes a time indicator that extends generally parallel to the vertical axis of the health-monitoring window and across the graph regions that are vertically stacked. The time indicator is movable along the horizontal axis of the health-monitoring window. The method also includes receiving user inputs for positioning the time indicator along the horizontal axis.

In an embodiment, a monitoring system is provided that is configured to monitor a condition of a patient. The monitoring system includes an operator display and a base unit configured to communicatively couple to a plurality of detection devices that detect physiological data of a patient. The monitoring system also includes a processor and a storage medium that is configured to store programmed instructions accessible by the processor. In response to execution of the programmed instructions, the processor is configured to receive the physiological data from the detection devices and present a health-monitoring window in the operator display. The health-monitoring window is based on the physiological data and includes a set of graph regions. Each of the graph regions of the set has a background and a parameter signal line appearing over the background. The parameter signal line is plotted with respect to horizontal and vertical axes of the health-monitoring window. The horizontal axis represents time and the vertical axis represents a patient parameter that is based on the physiological data. The parameter signal line appears to move along the horizontal axis as time progresses. For each of the graph regions of the set, the processor performs the following operations when executing the programmed instructions. The processor monitors the patient parameter associated with the corresponding graph region as the time progresses. The parameter signal line changes as the patient parameter changes. The processor also determines that the patient parameter of the corresponding graph region for a designated time is significant. The processor also automatically provides, in response to determining that the patient parameter is significant for the designated time, a reference color to the background for the designated time. The reference color includes at least one of a plurality of potential reference colors. The background for the designated time has a fixed position with respect to the parameter signal line such that an area of the background having the reference color moves along the horizontal axis with the parameter signal line as time progresses. Optionally, the graph regions of the set are positioned relative to one another to form a multi-parameter record of a patient. The respective areas of the graph regions of the set form a pattern that enables a user of the system to assess a health status of the patient. For example, the pattern may enable the user to more quickly diagnose one or more conditions of the patient.

In one or more aspects, the graph regions of the set are vertically stacked and the parameter signal lines of the graph regions are essentially synchronized. The health-monitoring window includes a time indicator that extends generally parallel to the vertical axis of the health-monitoring window and across the graph regions. The time indicator is movable along the horizontal axis of the health-monitoring window. The processor is configured to receive user inputs for positioning the time indicator along the horizontal axis.

Optionally, the health-monitoring window includes graph sub-regions that correspond to the graph regions. The graph sub-regions include local signal lines. The local signal lines are enlarged portions of the corresponding parameter signal lines of the graph regions where the time indicator intersects the corresponding parameter signal lines.

DETAILED DESCRIPTION

Figure 1:
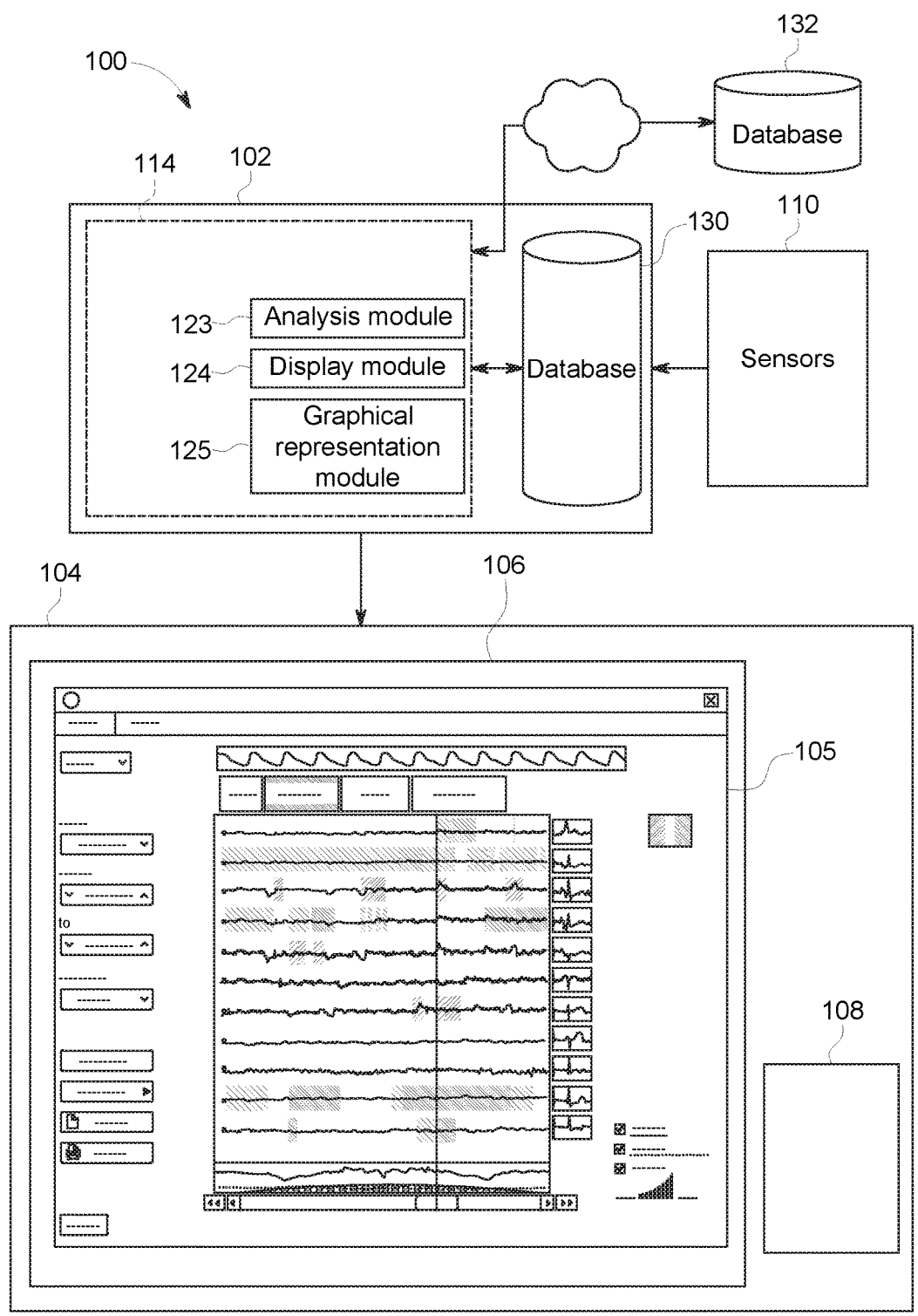
FIG. 1 is a block diagram of an exemplary system for displaying signal lines in accordance with an embodiment.

Exemplary embodiments that are described in detail below provide systems and methods that display one or more patient parameters based on physiological data that may be used to assess a health status of a patient. The physiological data includes values of the patient parameters or data that may be used to calculate values of patient parameters. In particular embodiments, the patient parameters are those used in electrocardiographic (ECG) analysis. For example, the patient parameters may correspond to the values of ST segment elevation or depression as derived from the ECG signal.

Although the various embodiments may be described in connection with electrocardiography, the systems and methods described herein are not limited to ECG analysis. Non-limiting examples of other types of monitoring that embodiments may be used in connection with include cardiotocographic analysis, electroencephalographic (EEG) analysis, electromyographic analysis, depth of sedation, among others. Embodiments may also analyze a plurality of patient parameters to determine a health index of the patient and display the health index to the user. The health index may inform a healthcare provider about a physiological deterioration of the patient. The health index may be based on, for example, a number of patient parameters (e.g., respiration rate, SpO2, pulse rate, and perfusion index). Embodiments may be used for more than one type of monitoring (e.g., ECG and a health index of the patient). Physiological information displayed by embodiments described herein may relate to, for example, electrical activity, blood pressure, heart rate, body temperature, and/or respiratory rate.

At least one technical effect of various embodiments includes providing a health-monitoring window that shows, over a designated time frame, when patient parameters have values that are significant or insignificant in a manner that enables a user (e.g., healthcare provider) to assess a health status of the patient more quickly than known monitoring systems. Another technical effect may include displaying a health-monitoring window that is easier to understand and apply than other displays of known monitoring systems.

Embodiments are configured to show a graph region having a signal line that represents a patient parameter over time. As used herein, a "signal line" includes a line plotted along a two-dimensional graph that represents a dynamic patient parameter as time progresses. For some implementations, the signal line may be referred to as a waveform, tracing or trace, or trend line. The signal line is not required to be a solid, continuous line throughout. For example, a single graph region may include multiple, overlapping signal lines. One or more of the signal lines may be a solid line and one or more of the other signal lines may be a dashed line. Different dashed lines may have different dashing patterns.

In some embodiments, the signal line is a compressed waveform that illustrates a trend of the patient parameter. Using ST-segment monitoring as an example, the signal line may be a compressed form of a continuous waveform that represents numerous heart beats over an extended period of time (e.g., several minutes, multiple hours, or one or more days). In such instances, discrete electrical stages or events of each heart beat (e.g., peaks and valleys of a wave) may not be identifiable due to the compression of the waveform. In other embodiments, however, the signal line may be a continuous waveform for a shorter period of time (e.g., 1-10 seconds) such that discrete electrical events of an individual heart beat can be identified.

A value of a patient parameter is determined to be "significant" based upon a predetermined standard. As used herein, the term "significant" does not require clinical significance. Instead, the term means that the value is noteworthy or worthy of the attention of a user of the system. The predetermined standard may be an algorithm and/or one or more predetermined conditions. In some cases, the predetermined standard is an established standard within a medical field. In other cases, the predetermined standard may be proprietary. In some cases, the predetermined standard may be modified by the user of the system or entirely provided by a user of the system. For example, the user may change an upper limit to which the patient parameter will be compared, change a lower limit to which the patient parameter will be compared, and/or change an operating range to which the patient parameter will be compared. Optionally, the upper limit, the lower limit, and/or the operating range may have default values when the system is initially executed. In other embodiments, the predetermined standards may be entirely provided by the user. For example, the user may select a formula or enter a formula into the system. The formula may use the patient parameter, among other parameters or factors, as an input to determine whether the patient parameter is significant.

To illustrate some examples, a value may be significant if one or more of the following occurs: (a) the patient parameter has exceeded a designated value (e.g., exceeded an upper limit); (b) a patient parameter is below a designated value (e.g., below a lower limit); or (c) a patient parameter is not within a designated operating range, which may also be referred to as out-of-range. In some embodiments, a value is significant if (a), (b), or (c) are satisfied and if other conditions are satisfied. For example, a value may be significant only if (a), (b), or (c) are satisfied and a signal quality of the patient parameter is sufficient and/or other patient parameters have exceeded a designated value, fallen below a designated value, or are within a designated operating range. In some embodiments, a value is significant only if the patient parameter has satisfied (a), (b), or (c) for at least a minimum amount of time. For example, a value of a patient parameter may not be determined to be significant until the value has been above the upper limit for at least five seconds. Similarly, a value of a patient parameter may not be determined to be significant until the value has been below the lower limit for at least five seconds.

Alternatively or in addition to one or more of the above, a value may be significant only if the patient parameter has satisfied (a), (b), or (c) for at least a minimum number of events. For example, a value of a patient parameter may not be determined to be significant until the value has been above the upper limit for at least three heart beats. Similarly, a value of a patient parameter may not be determined to be significant until the value has been below the lower limit for at least three heart beats.

In some embodiments, a value may be significant if one or more of the following occurs: (a) the patient parameter has not exceeded a designated value (e.g., has not exceeded an upper limit); (b) a patient parameter is above a minimum value (e.g., above a lower limit); or (c) a patient parameter is within a designated operating range.

It should be understood that the above predetermined standards are examples of specific embodiments and other predetermined standards may be used for other embodiments. Other predetermined standards may include more complex algorithms that are based upon a number of patient parameters. The predetermined standards may also be based on other variables, including information that is not a parameter monitored by the system. For example, the predetermined standards may be a function of patient information (e.g., height, weight, medical history).

Accordingly, the predetermined standard for determining whether a patient parameter is significant may be a simple condition (e.g., a comparison to a limit) or may be a more complex calculation (e.g., an algorithm having multiple variables). The predetermined standard may be set by the system (e.g., stored within software), modified by the user, or entirely provided by the user. For embodiments that display multiple patient parameters, each of the patient parameters may have a respective predetermined standard that may or may not be different from the predetermined standards of other patient parameters.

In particular embodiments, multiple patient parameters are represented in the health-monitoring window to form a multi-parameter record over an extended period of time (or time frame). By way of example, the time frame may be at least one minute, at least ten minutes, at least twenty minutes, at least one hour, at least three hours, or more. A healthcare provider may be able to simultaneously view and consider the significant moments of the multiple patient parameters over the time frame in order to assess a health status of the patient. Compared to known monitoring systems, embodiments may enable a quicker identification of the health status by using a display that requires less training. As described below, the intuitive display may be selected or modified by the user.

The systems and methods set forth herein may present (e.g., show or display) a historical record of the patient. The historical record may indicate moments within an extended period of time in which the patient had a healthy status and, if applicable, may show moments in which a patient parameter is significant (e.g., concerning or worthy of a healthcare provider's consideration). The significant moments may be identified using predetermined standards. In some embodiments, the system and methods are directed to assessing a cardiac condition of a patient. The physiological data received by the system is ECG data. Embodiments may simultaneously show the histories of multiple ECG leads to assess the cardiac condition of the patient. More specifically, embodiments may enable the healthcare provider to quickly identify when and which ECG leads have significant values and for how long the ECG leads had significant values. By way of example, embodiments may facilitate identifying the onset of an anterior ST segment elevation myocardial infarction (or anterior STEMI).

As used herein, the term "physiological data" (or "physiological signals") may include only one type of data (or signals) or multiple types of data (or signals). For examples, physiological data may include physiological data relating to a first type (e.g., ECG data) and physiological data relating to a second type (e.g., EEG data, heart rate, pulse oximetry, etc.). The physiological data may be obtained by detection devices. Non-limiting examples of a detection device include an electrode (e.g., ECG lead), a pulse oximeter, a heart rate monitor, a detector that monitors motion of the patient (e.g., accelerometer or global positioning system (GPS) device), a non-invasive blood pressure (NIBP) monitor (e.g., NIBP cuff), a respiratory monitor, and the like.

As used herein, an element or step recited in the singular and proceeded with the word "a" or "an" should be understood as not excluding plural of said elements or steps, unless such exclusion is explicitly stated. For example, the phrase "a processor" may include a single processor, a multi-core processor, or a plurality of processors. If a plurality of processors are used, the plurality of processors may be found within a single unit (e.g., computer) or may be distributed throughout a system, such as in multiple units. If one processor is used, the claims may recite the processor as "only a single processor."

As used herein, the phrase "a health-monitoring window including a set of graph regions" (and similar phrases) does not necessarily mean each and every graph region that the window may have. For example, a health-monitoring window may include other graph regions that are not part of the set of graph regions.

Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when a feature is described as being based on a parameter or being a function of a parameter, the term "based on" or "function of" should not be interpreted as the parameter being the sole parameter or primary parameter, but may include the possibility that the element is also based on other parameters.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

FIG. 1 is a block diagram of an exemplary system 100. The system 100 is configured to present information to a user for assessing a health status of a patient (e.g., diagnosing a condition of the patient). The user may be a healthcare provider (e.g., doctor, nurse, or other qualified person). In some embodiments, the user may also be the patient. As used herein, the term "patient" means an individual that is being monitored by the system 100. The individual is not necessarily a human as some embodiments may be used to monitor animals. The system 100 may be located on-site in which at least some elements of the system 100 are located within the same room as a patient and other optional elements may be located in the same building. In other embodiments, the system 100 may have some elements that are on-site and other elements that are remotely located relative to the patient. In some embodiments, the system 100 is configured to store and communicate historical data that is not presently being monitored. For example, the historical data may include an electrocardiogram that was acquired a day earlier.

The system 100 includes a user interface 104 and a computing system or device 102 that is communicatively coupled to the user interface 104. The user interface 104 may include instruments (e.g., operator display), hardware, and software (or a combination thereof) that permit the system 100 to display information to the user and, in some embodiments, permit the user to provide user inputs or selections. The user interface 104 may include an operator display 106 (e.g., monitor, screen, touchscreen, and the like) and an input device 108 (e.g., keyboard, computer mouse, tracking button, touchpad, touchscreen, and the like) that is capable of receiving and communicating user inputs to the computing system 102. In some embodiments, a device constituting the input device 108 may also be the device constituting the operator display 106. For example, the operator display 106 may include a touch-sensitive screen. The operator display 106 may be configured to show a viewable area that includes a health-monitoring window 105, which is described in greater detail below. The health-monitoring window 105 may occupy the entire viewable area or only a portion of the viewable area. In particular embodiments, the health-monitoring window 105 occupies the entire viewable area. The user interface 104 may also be configured to query or prompt the user of the system 100 for designated information.

The system 100 may include a plurality of discrete components that are operably coupled to one another. The discrete components may or may not be located near each other. In some embodiments, the computing system 102 may constitute a base unit or on-site monitor 102 that is positioned within the same room as a patient. For example, the base unit 102 may be positioned adjacent to the patient's bed. The base unit 102 communicatively couples to detection devices 110 (e.g., electrodes) that receive physiological data relating to the patient. In such instances, the base unit 102 may include the operator display 106. For example, the operator display 106 may include a screen that is disposed on the base unit 102. The screen may have the health-monitoring window 105 as set forth herein that is viewable by the healthcare provider while attending to the patient.

Alternatively, the computing system 102 may be, for example, a desktop computer or portable communication device (e.g., a laptop computer, tablet computer, smartphone). In particular embodiments, the system 100 includes detection devices 110 that are configured to detect physiological data from an individual (e.g., a patient) and communicate the physiological data to the computing system 102. The detection devices 110 are sensors (or detectors or transducers) that observe the patient and communicate physiological data to the computing system 102 based on the observations. In particular embodiments, the detection devices 110 are electrodes configured to detect electrical activity within the patient, such as the electrical activity of the heart and/or brain. Alternatively or in addition to electrical activity, the detection devices 110 may be configured to detect other physiological data, such as a heart rate, body temperature, blood pressure, respiratory rate, intrauterine pressure, peripheral capillary oxygen saturation (SpO2), etc.

The detection devices may be directly connected through wires and cables to the computing system 102. Alternatively, the detection devices may be wirelessly coupled to the computing system 102. The wireless communication may be in accordance with a wireless technology standard that is configured to exchange data over short distances (e.g., such as Bluetooth). However, a variety of communication standards may be used.

The system 100 detects, analyzes, and displays patient parameters based on the physiological data. The system 100 may be particularly suitable for displaying multi-parameter records. As an example, the multi-parameter records may be visually similar or identical to ECGs or EEGs used by healthcare providers to assess a health status of the patient. The system 100 may detect electrical activity of the heart over a period of time using electrodes placed on a patient's body (e.g., chest, limbs, head). The electrodes detect the electrical changes on the skin that arise from the heart muscle depolarizing during each heartbeat or, alternatively, from current in the neurons of the brain. In a conventional 12-lead ECG, ten electrodes are placed on the patient's limbs and on the surface of the chest. The overall magnitude of the heart's electrical potential is then measured from twelve different angles ("leads") and is recorded over a period of time. As such, an overall magnitude and direction of the electrical depolarization may be captured throughout multiple cardiac cycles. Although embodiments may be suitable for a conventional 12-lead ECG, embodiments may also be suitable for a fewer number of leads or a greater number of leads.

The computing system 102 may include or be part of a server system, a workstation, a desktop computer, a laptop computer, or a personal device, such as a tablet computer or a smartphone. However, the above are only examples and the computing system 102 may be other types of systems or devices. In the illustrated embodiment, the computing system 102 includes a system controller 114, which may comprise a controller, processor, or other logic-based device. The system controller 114 may have or be communicatively coupled to modules for performing methods as described herein. The modules may include an analysis module 123, a display module 124, and a graphical representation module 125. Each of the modules 123-125 may be a part of another module or include another module. For example, the graphical representation module 125 may be a part of the display module 124. In addition to the above, there may be several other modules or sub-modules of the system controller 114 that are not shown. Each of the modules 123-125 may be communicatively coupled to a memory or database 130 and/or communicatively coupled to a remote memory or database 132 via, for example, the internet or other communication network. Although the database 130 is shown as being shared by the modules 123-125, each module 123-125 may have a separate memory or database.

The analysis module 123 is configured to receive the physiological data from the detection devices 110 and analyze the physiological data. In some embodiments, the physiological data from one detection device 110 may represent a patient parameter. For example, the physiological data from a pulse oximeter may directly correspond to an oxygen level in the blood. In other embodiments, a patient parameter may be based on the physiological data from two or more detection devices. For example, values of at least some ECG leads may be based on the physiological data of two or more electrodes. Accordingly, the analysis module 123 may also process the physiological data from one or more detection devices 110 to determine corresponding patient parameters.

In some embodiments, the analysis module 123 may also analyze the physiological data and/or the patient parameters to identify events-of-interest. For example, the analysis module 123 may analyze the physiological data and/or the patient parameters to determine when an alarm condition, such as an ischemic event, has occurred. As another example, the analysis module 123 may analyze the physiological data and/or the patient parameters to determine when a patient has moved. The analysis module 123 may use one or more algorithms to identify the events-of-interest. If an event-of-interest is identified, the analysis module 123 may communicate this information to the display module 124 and/or the graphical representation module 125 to notify the user.

The display module 124 may operate in conjunction with the analysis module 123 and/or the graphical representation module 125. For example, the graphical representation module 125 may store graphical objects that represent patient parameters, such as the indicators described below. The display module and/or the graphical representation module 125 may generate graphics that correspond to the data provided by the analysis module 123. For example, the display module and/or the graphical representation module 125 may generate a graph region having a background and signal line as described below based on the data provided by the analysis module 123. The patient parameters may be monitored by the analysis module 123 to identify when a patient parameter is significant. As used herein, the term "monitor" includes continuously analyzing the physiological data and/or patient parameters or analyzing the physiological data with a suitable frequency. For example, the physiological data may be monitored by analyzing the physiological data, on average, at least every minute, at least every 30 seconds, at least every 20 seconds, at least every 10 seconds, or at least every 5 seconds. The graphical representation module 125 may also be configured to store various graphical objects that provide the overall appearance of a health-monitoring window.

The databases 130 and 132 may store data that can be retrieved by the components or modules of the system 100 and other remotely located systems through the internet or other communication network. The databases 130 and 132 can store data that the modules 123-125 require in order to accomplish the functions of the modules 123-125. For example, the databases 130 and 132 can store the physiological signals obtained from the detection devices 110.

The modules 123-125 (and the system controller 114) include one or more processors. A processor may include a microprocessor or other logic-based device. The processor may be or be part of a controller or microcontrollers. A processor operates based on instructions stored on a tangible and non-transitory computer readable storage medium. A processor may operate based on hardwired instructions. The databases 130 and 132 can be or include electrically erasable programmable read only memory (EEPROM), simple read only memory (ROM), programmable read only memory (PROM), erasable programmable read only memory (EPROM), FLASH memory, a hard drive, or other type of computer memory.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data and provide output data in the form of a health-monitoring window, among other things. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

Figure 2:
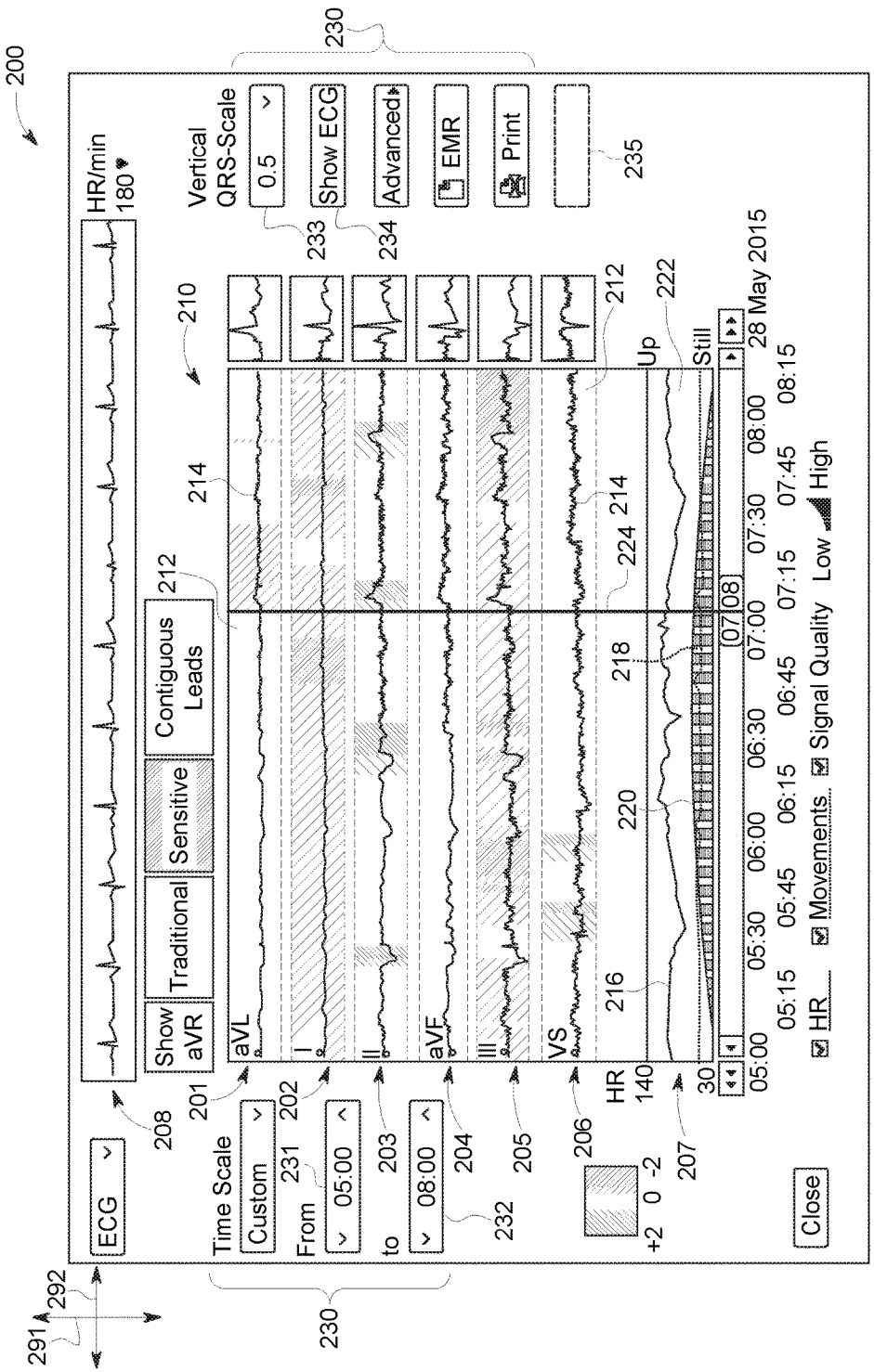
FIG. 2 illustrates a health-monitoring window that may be presented to a user of the system of FIG. 1.

FIG. 2 illustrates a health-monitoring window 200 in accordance with an embodiment. The health-monitoring window 200 is configured to be presented in an operator display, such as the operator display 106 (FIG. 1). The health-monitoring window 200 may span an entirety of a viewable area along the operator display. In other embodiments, however, the health-monitoring window 200 may only span a portion of the viewable area. The health-monitoring window 200 is oriented with respect to a vertical axis 291 and a horizontal axis 292 of the health-monitoring window 200.

The health-monitoring window 200 includes information that may be used by the user (e.g., healthcare provider) to monitor and assess a condition of the patient. In an exemplary embodiment, the condition is a cardiac condition. For example, the user may be able to determine whether an STEMI has begun. However, embodiments may be configured to present information for determining other cardiac conditions or other conditions of a patient. The information is based, at least in part, on physiological data received from the patient. The physiological data may be from a current or present session of the patient or from a session that has already been entirely recorded. The physiological data is from detection devices.

The health-monitoring window 200 includes graph regions 201-208. Two or more of the graph regions 201-208 may be related to one another such that a condition of the patient is essentially made by considering the two or more graph regions as a group. For example, the graph regions 201-206 correspond to patient parameters (e.g., ECG leads) that may be used to assess the condition of a heart. The graph regions 201-206 may be collectively referred to as a set or group 210. Each of the graph regions 201-206 has a background 212 and a parameter signal line 214 appearing over the background 212.

In particular embodiments, a multi-parameter record is formed during a monitoring session. The multi-parameter record includes the graph regions 201-206 over a designated period of time. The graph regions 201-206 are positioned relative to one another to form the multi-parameter record. The positions of the graph regions 201-206 may be consistent with established standards for the conditions sought to be diagnosed. By way of example, the graph regions 201-206 are vertically stacked (or stacked along the vertical axis 291) and the parameter signal lines 214 of the graph regions 201-206 are essentially synchronized. As such, the values of the patient parameters that intersect a common vertical line (such as a time indicator) represent the values of the different patient parameters that occur at essentially the same time.

In some embodiments, the positions of the graph regions 201-206 may be selected or changed by the user of the system. A user may prefer a certain arrangement of the graph regions 201-206 over other arrangements when assessing the health status. For example, the user may believe that he or she may more quickly recognize a pattern within the multi-parameter record when the graph regions 201-206 are arranged in a designated order. As such, embodiments may enable the user to move the graph regions 201-206 relative to one another. For example, a user may select a graph region and drag the graph region to a different position (e.g., at a top position, bottom position, or in between two other graph regions). The system may automatically move the other graph regions.

The parameter signal lines 214 are plotted with respect to the horizontal and vertical axes 292, 291. Each of the parameter signal lines 214 is based on the physiological data and may correspond to a patient parameter, including more than one patient parameter. With respect to each of the graph regions 201-206, the horizontal axis 292 of the health-monitoring window 200 is associated with time, and the vertical axis 291 is associated with the patient parameter that is based on the physiological data. More specifically, different locations of the parameter signal line 214 along the horizontal axis 292 correspond to different moments in time, and different locations of the parameter signal line 214 along the vertical axis 291 are associated with different values of the patient parameter of the corresponding graph region. However, it should be understood that each of the graph regions may have its own horizontal axis (or X-axis) and vertical axis (or Y-axis) that are associated with time and parameter values, respectively.

As shown, the patient parameters represented by the graph regions 201-206 include the leads from ECG data. The leads are derived from electrodes positioned on the patient. In 12-lead electrocardiograms, the patient parameters include the six chest leads that detect the depolarization wave in the frontal plane. These may also be referred to as the precordial leads and are V1, V2, V3, V4, V5, and V6. Each of the chest leads corresponds to an electrode that has a designated position on the patient's chest. The patient parameters also include extremity leads I, II, III, aVL, and aVF. The extremity leads are derived from electrodes that are positioned on the left and right arm and left and right legs. In some embodiments, each of the precordial leads and the extremity leads is shown. In other embodiments, only some of the precordial leads and the extremity leads are shown. For example, FIG. 2 shows aVL, I, II, aVF, III, and V5. As described above, the number and order of the graph regions (i.e., leads) that are presented may be selected by a user of the system. In some cases, the names or labels of the different patient parameters may be selected and/or modified by the user.

As described herein, embodiments may be configured to identify when a patient parameter is significant and indicate those time periods by changing a color of the background. Although the patient parameters in the illustrated embodiment correspond to patient parameters that are detected during ECG sessions, other embodiments may display patient parameters that are based on other physiological data and that may be used in assessing a patient's health status.

The graph region 207 includes information regarding multiple patient parameters. For example, the graph region 207 illustrates a parameter signal lines 216, 218 and a signal quality level 220 over a background 222. The parameters signal lines 216, 218 correlate to respective patient parameters. More specifically, the parameters signal lines 216, 218 correspond to respective the heart rate (HR) and movements of the patient. The signal quality level 220 represents a signal quality associated with designated patient parameters. In FIG. 2, the signal quality level 220 indicates the signal quality of the patient parameters represented by the graph region regions 201-206. In the illustrated embodiment, the user is enabled to display the parameter signal lines 216, 218, and 220 by marking boxes (labeled "HR" and "Movements" and "Signal Quality," respectively). If the boxes are not marked, the health-monitoring window 200 may not show the parameter signal lines 216, 218, and 220.

Also shown, the health-monitoring window 200 may include at least one time indicator 224 that extends generally parallel to the vertical axis 291 of the health-monitoring window 200 and across the graph regions 201-206 of the set 210. In some embodiments, the time indicator 224 is movable along the horizontal axis 292. A system that displays the health-monitoring window 200 may be configured to receive user inputs for positioning the time indicator 224 along the horizontal axis 292. As described herein, the health-monitoring window 200 may show enlarged views of the parameter signal lines 214 based on a location of the time indicator 224. The enlarged views may be caused by a user input, such as a screen touch at a designated area or a mouse click while the mouse cursor is located at the designated area.

The health-monitoring window 200 also includes a plurality of user-selectable elements 230. In FIG. 2, the user-selectable elements 230 include a starting time selection element 231 and an end time selection element 232. The starting time selection element 231 and the end time selection element 232 enable a user to select the desired time period of the monitoring session. The user-selectable elements 230 also include a scale selection element 233 that enables a user to select an aspect ratio of the parameter signal lines. A user-selectable element 234 is also shown that, when selected by the user, presents an electronic chart (e.g., electrocardiogram) as described below. Also shown, the health-monitoring window 200 includes a color legend 240.

Optionally, a user-selectable element 235 may be presented for changing a value of the upper limit or a value of the lower limit to which the patient parameters will be compared may be selected by the user. For example, a user may select the user-selectable element 235. A screen (not shown) may then be shown to the user. The screen may include options for changing the predetermined standards that are used to identify whether a value is significant. For example, the screen may allow the user to change a value of the lower limit or change a value of the upper limit for those patients that have had a prior ischemic event. Alternatively or in addition to the above, a user-selectable element for changing the predetermined standard of a graph region may be requested individually for each graph region. For example, using a mouse, the user may position a cursor over a graph region and "right-click" with the mouse. A drop-down list of options may appear adjacent to the cursor. The list of options may include a "change standards" option. By selecting the option, the user may be directed to a pop-up screen that enables the user to change the predetermined standards for the patient parameter where the cursor was located.

Figure 3:
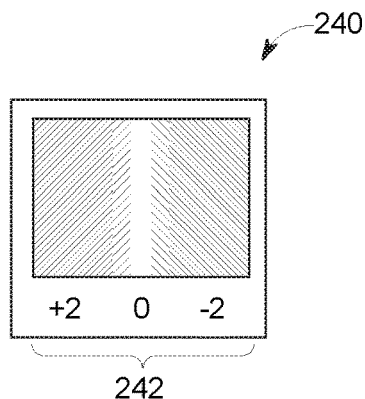
FIG. 3 illustrates a color legend that may be presented to a user of the system of FIG. 1 in the health-monitoring window.

FIG. 3 includes the color legend 240. As described herein, embodiments are configured to provide a reference color to the background 212 (FIG. 2) of the graph regions 201-206 (FIG. 2) for a designated time. The reference color may apply to only a portion of the background 212 for the designated time, or an entirety of the background 212 for the designated time. The reference color may be selected from a plurality of potential reference colors to represent moments (or time periods) in which the patient parameter is significant. As used herein, the term "designated time," may correspond to only a single visible unit in the graph region (e.g., 0.05 seconds, 0.10 seconds) or may include greater time periods, such as multiple seconds or minutes. When the patient parameter is not significant, the background may have a "background color" or "standard color." The background color may be, for example, white or black. However, other colors that are visually different from the potential reference colors may also be used. The potential reference colors are visibly distinct from the background color so that a user may visually recognize when values of the patient parameter are significant. In particular embodiments, the potential reference colors are visibly distinct from the background color so that a user may simultaneously consider multiple patient parameters over an extended period of time.

The color legend 240 shows the potential reference colors for viewing by a user of the system. The color legend 240 may also include a scale 242 that associates values or degrees with the potential reference colors. In FIG. 3, the scale 242 is designed for applications that are used to diagnose STEMI. For example, the scale ranges from +2 to −2, which are values that correspond to the number of millimeters that a signal line from a conventional ECG is above or below a predetermined value. It should be understood, however, that embodiments may have different scales. Moreover, it should be understood that the scale is not required to indicate numbers. For example, the scale may indicate different levels or degrees through words. For example, the values +2, 0, and −2 in FIG. 3 may be replaced with the words "above," "average," and "below", respectively. In other embodiments, the color legend 240 does not include a scale.

Because FIG. 3 is a black-and-white line drawing, the different colors are represented by different hatching. To illustrate one example, the color associated with 0 or values close to 0 (e.g., 0.2 to −0.2) may be white. The color associated with values to the left of 0.2 (or values greater than 0.2) may be red, and the color associated with values to the right of 0 (or values less than −0.2) may be blue. The color may gradually change based on how much the patient parameter is significant. More specifically, the color may gradually change based on how much the value of the patient parameter differs from 0. For example, as the value increases from 0.2 to +2, the color becomes a darker red. As the value decreases from −0.2 to −2, the color becomes a darker blue. Although the above example uses the colors red and blue, different colors may be used in other embodiments.

In some embodiments, the reference color may be selected from a relatively small number of discrete base colors (e.g., two colors not including the background color) and have a designated transparency. The discrete base color and designated transparency are a function of a value of the patient parameter. In FIG. 3, the reference color includes one of two base colors (e.g., red or blue) and has a transparency percentage (e.g., 0%, 20%, 40%, 60%, 80%). As such, the number of potential reference colors in FIG. 3 is ten in which the background color (e.g., white) is positioned two groups of five reference colors. More specifically, the reference colors to the left of the background color include, in order from left to right, red at 0% transparency, red at 20% transparency, red at 40% transparency, red at 60% transparency, and red at 80% transparency. The reference colors to the right of the background color include, in order from left to right, blue at 80% transparency, blue at 60% transparency, blue at 40% transparency, blue at 20% transparency, and blue at 0% transparency. Each of the reference colors is associated with a designated value or range of values for the corresponding patient parameter. For example, red at 0% transparency is associated with +1.8 or above, and red at 20% transparency is associated with +1.6 to +1.2.

Accordingly, the reference color is a function of a base color and, optionally, at least one of a transparency level or a color characteristic (e.g., hue, tint, shade, saturation, brightness, or chroma). For embodiments in which the patient is being monitored in real time, the reference color may be applied to the vertical column corresponding to a single visible unit of time. For embodiments in which the patient parameters are not analyzed in real time, the reference color may be applied to larger areas. In some embodiments, the reference color for a designated time includes more than one base color. For example, the reference color may include hatching having some stripes as one base color and other stripes as other base colors. As another example, the reference color may change as the value of the patient parameter moves further away from an average value or expected value.

The reference color may be selected from a larger number of discrete colors (e.g., six colors or less) with a greater or fewer number of possible transparency percentages. Yet in other embodiments, the reference colors may be selected from a number of discrete colors only, without a change in transparency level or color characteristics. For example, the discrete colors may include (in order from left to right) red, orange, yellow, blue, indigo, and violet. In this example, the background color may separate yellow and blue. Yet in other embodiments, the reference colors may be selected from any point along the visible color spectrum. Accordingly, a variety of color systems having a plurality of potential colors may be used for indicating a value or other state of the patient parameter.

In certain embodiments, the reference color (or the base color of the reference color) is selected from the potential reference colors based on whether the patient parameter is above an upper limit or below a lower limit. The reference color above the upper limit and the reference color below the lower limit may have respective wavelengths that are separated by a designated amount along the visible spectrum. This designated amount (or difference between the respective wavelengths) may be, for example, at least 30 nanometers (nm), at least 40 nm, at least 50 nm, or at least 60 nm. In more particular embodiments, the difference between the respective wavelengths of the different reference colors may be, for example, at least 70 nm, at least 75 nm, or at least 80 nm.

In certain embodiments, the reference color (or the base color of the reference color) associated with a patient parameter that is above the upper limit and the reference color associated with a patient parameter that is below the lower limit may be selected from separate color spectrums. In such embodiments, the reference colors may change within the designated color spectrum based on the patient parameter. For example, the reference color may become more red or darker (e.g., the wavelengths may increase) as the patient parameter becomes more severe above the upper limit. The reference color may become more blue (e.g., the wavelengths may decrease) as the patient parameter becomes more severe below the lower limit. The color spectrums may be separated by at least 30 nm, at least 40 nm, at least 50 nm, or at least 60 nm. In more particular embodiments, the difference between the separate color spectrums may be, for example, at least 70 nm, at least 75 nm, or at least 80 nm.

Figure 4:
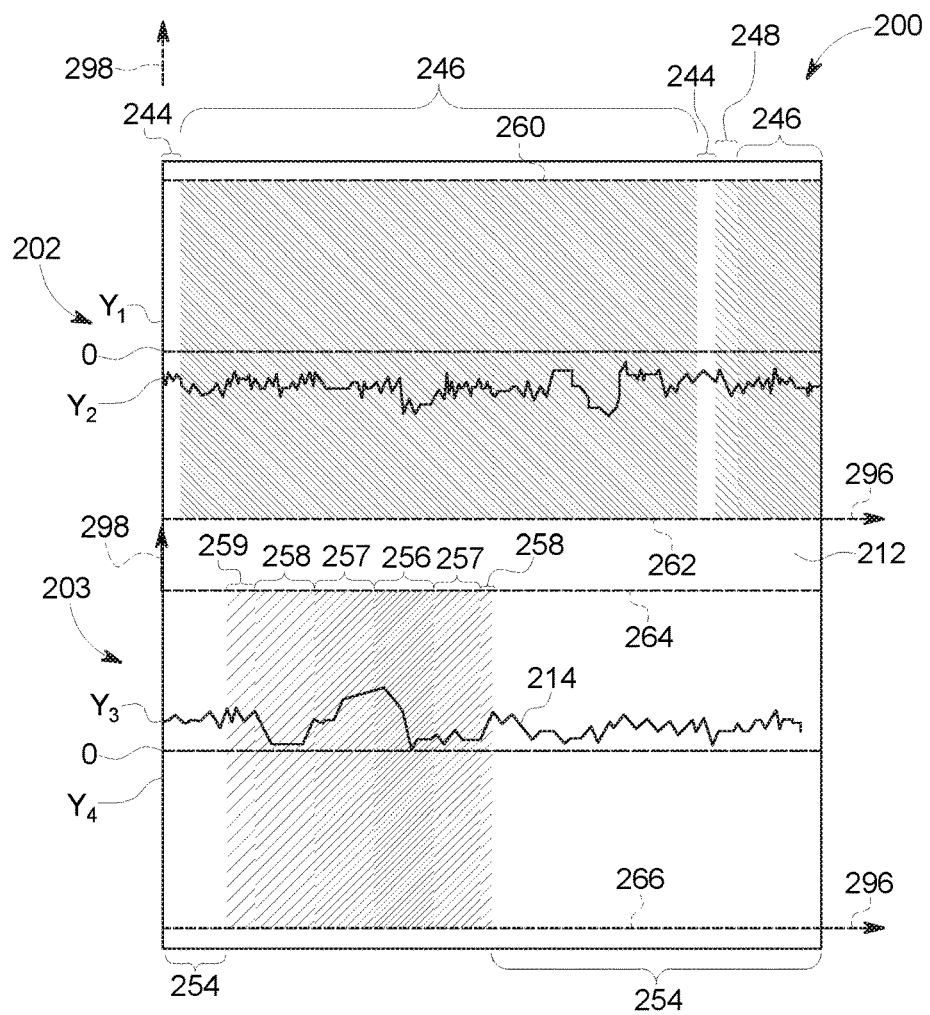
FIG. 4 shows graph regions of the health-monitoring window that may be presented to a user of the system of FIG. 1.

FIG. 4 is an enlarged view of the health-monitoring window 200 that includes portions of the graph regions 202, 203. In the illustrated embodiment, the background 212 of the graph region 202 has designated areas 244, which may be referred to as insignificant areas, that have the background color (e.g., white). The background 212 of the graph region 202 also has designated areas 246, 248, which may be referred to as significant areas. The areas 246, 248 have respective reference colors. As described above, the reference color is a function of the patient parameter and includes a base color and, optionally, at least one of a transparency level or a color characteristic. For example, the areas 246 may have a reference color including a base color of blue and a transparency level of 20%. The area 248 may have a reference color including a base color of blue and a transparency level of 40%.

In the illustrated embodiment, the background 212 of the graph region 203 has designated areas 254, which may be referred to as insignificant areas, that have the background color (e.g., white). The background 212 of the graph region 203 also has designated areas 256, 257, 258, 259 which may be referred to as significant areas. The areas 256-259 have respective reference colors. As described above, the reference color is a function of a base color and, optionally, at least one of a transparency level or a color characteristic. For example, the area 256 may have a reference color including a base color of red and a transparency level of 20%. The areas 257 may have a reference color including a base color of red and a transparency level of 40%. The areas 258 may have a reference color including a base color of red and a transparency level of 60%. The area 259 may have a reference color including a base color of red and a transparency level of 80%.

The parameter signal line is a dynamic line that is capable of constantly changing. The parameter signal line may be plotted with respect to horizontal and vertical axes 296, 298 of the respective graph region. The horizontal and vertical axes 296, 298 are parallel to the horizontal and vertical axes 292, 294, respectively, of the health-monitoring window 200. The parameter signal line 214 appears to move along the horizontal axis 296 (or the axis 292) as time progresses. As the parameter signal line 214 appears to move along the horizontal axis 296, the background 212 has a fixed position with respect to the parameter signal line 214 such that an area of the background having the reference color appears to move along the horizontal axis 292 with the parameter signal line 214 as time progresses. In other words, the reference color applied to time $t_1$ will move with the vertical position of the parameter signal line 214 at time $t_1$. The reference color applied to time $t_2$ will move with the vertical position of the parameter signal line 214 at time $t_2$.

In the embodiment of FIG. 4, the graph region 202 has a top horizontal line 260 and a bottom horizontal line 262, the graph region 203 has a top horizontal line 264 and a bottom horizontal line 266. The bottom horizontal lines 262, 266 coincide with the horizontal axis 296 of the respective graph region. The top and bottom horizontal lines 260, 262 may be visually indicated with a dashed line or a solid line. In other embodiments, the horizontal lines 260, 262 may be visually indicated by a border between two different areas having two different colors. The reference color or background color for each designated time extends between the top horizontal line 260 positioned above the parameter signal line 214 and the bottom horizontal line 262 positioned below the parameter signal line 214. In particular embodiments, the parameter signal line 214 is visible over the background 212 that has the reference color.

Similarly, the top and bottom horizontal lines 264, 266 may be visually indicated with a dashed line or a solid line. In other embodiments, the horizontal lines 260, 262 may be visually indicated by a border between two different areas having two different colors. The reference color or background color for each designated time extends between the top horizontal line 264 positioned above the parameter signal line 214 and the bottom horizontal line 266 positioned below the parameter signal line 214. In particular embodiments, the parameter signal line 214 is visible over the background 212 that has the reference color.

In the illustrated embodiments, the horizontal lines 260, 262, 264, 266 appear as top and bottom borders of the respective graph regions. In other embodiments, however, the horizontal lines 260, 262, 264, 266 may not be top and bottom borders of the respective graph regions. Instead, the horizontal lines 260, 262, 264, 266 may be located within the respective graph regions.

In other embodiments, such as the embodiments shown with respect to FIGS. 5-7 and 9-11, only a portion of the background for the designated time has the reference color. The reference color may exist between the parameter signal line and a horizontal line of the graph region. The parameter signal line may be a border of the background that has the reference color.

Optionally, the graph regions may indicate reference values along the vertical axis 298. For example, the graph region 202 includes reference values $Y_1$, 0, and $Y_2$. The graph region 203 includes reference values $Y_3$, 0, and $Y_4$. In some embodiments, the reference values may include the upper limits and/or lower limits that are used to determine whether a value of the patient parameter is significant. Alternatively or in addition to indicating the limits, the reference values along the axis 298 may include a designated series (e.g., every change in 0.2 may be labeled).

Figure 5:
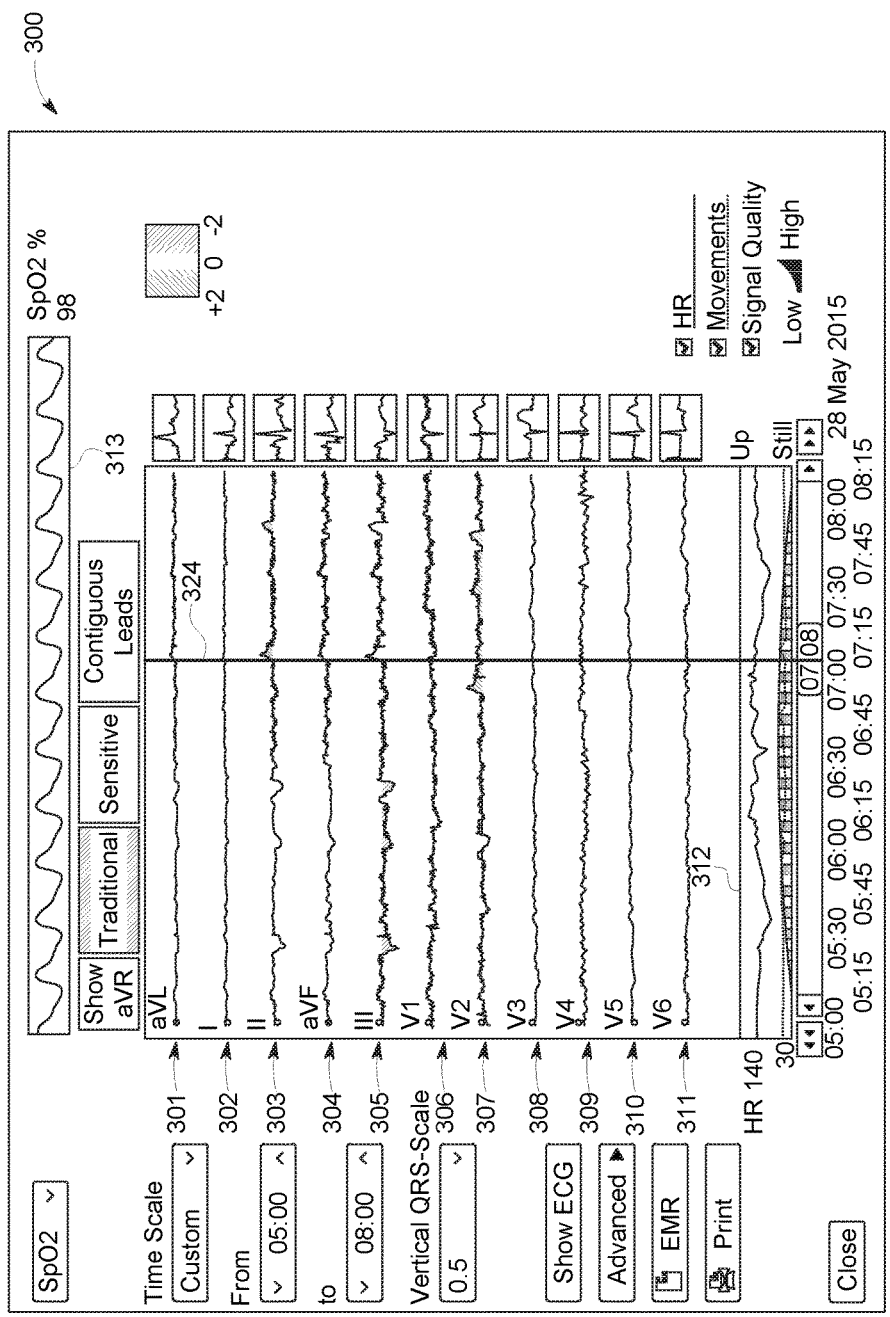
FIG. 5 illustrates a health-monitoring window that may be presented to a user of the system of FIG. 1 in accordance with an embodiment.

FIG. 5 illustrates an exemplary health-monitoring window 300 in accordance with an embodiment. The health-monitoring window 300 may include features that are similar or identical to the features of the health-monitoring window 200 (FIG. 2). As shown, the health-monitoring window 300 includes graph regions 301-311 that are similar to the graph regions 201-206. Graph regions 312, 313 are identical to the graph regions 207, 208, respectively. The health-monitoring window 300 may also include user-selectable elements and a color legend that are identical to features of the health-monitoring window 200.

Figure 6:
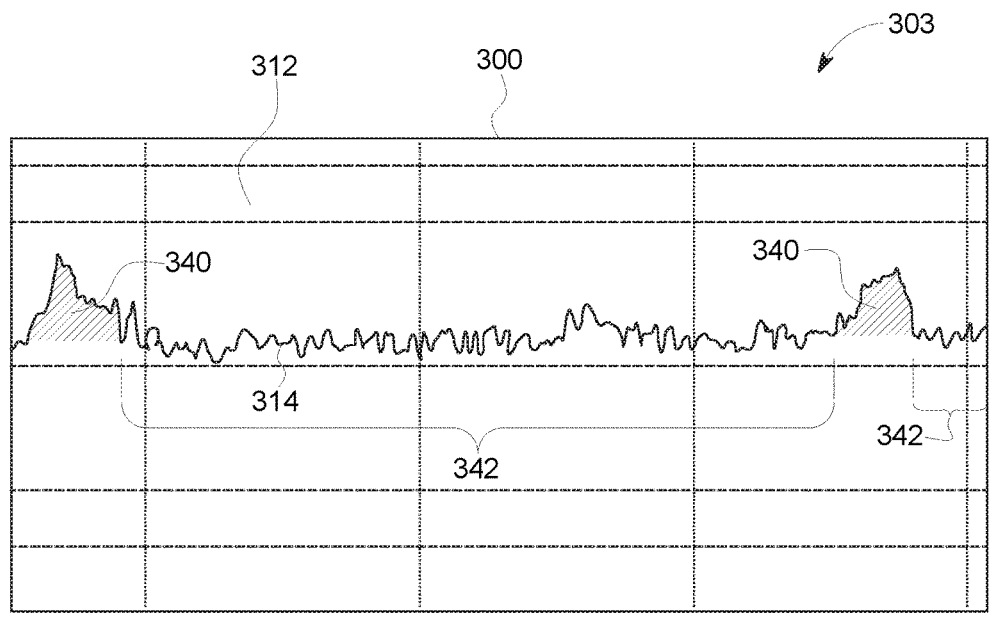
FIG. 6 illustrates a graph region of the health-monitoring window of FIG. 5 that may be presented to a user of the system of FIG. 1.
Figure 7:
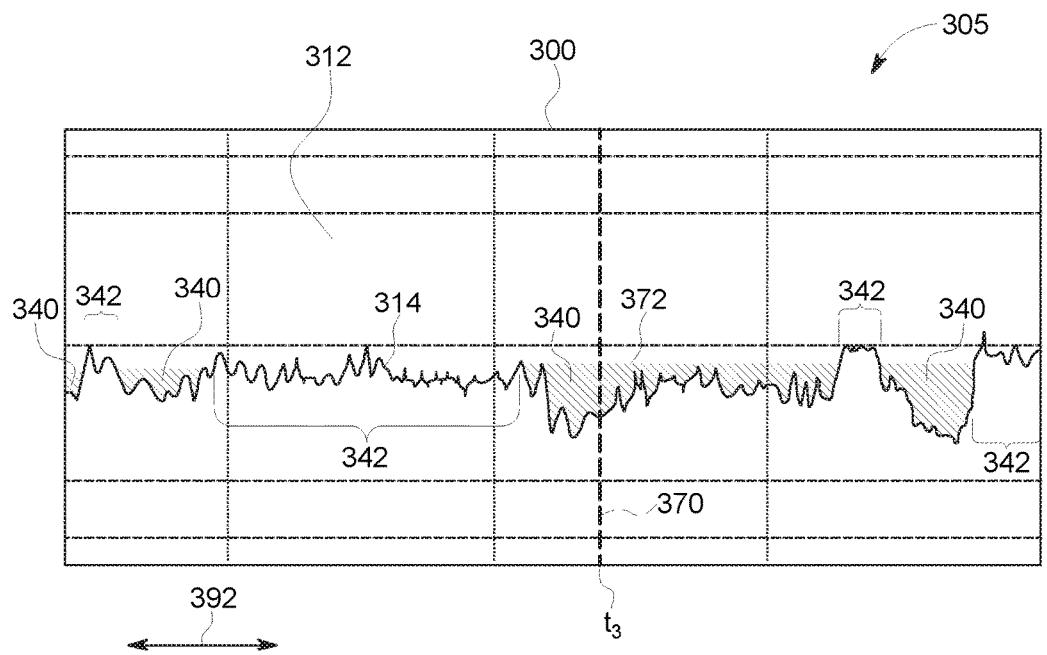
FIG. 7 illustrates a graph region of the health-monitoring window of FIG. 5 that may be presented to a user of the system of FIG. 1.

FIGS. 6 and 7 illustrate enlarged portions of the graph regions 303, 305 of the health-monitoring window 300. The portions of the graph regions 303, 305 are not synchronized (e.g., do not correspond to the same time periods). Each of the graph regions 303, 305 has a background 312 and a parameter signal line 314. The background 312 in each of the graph regions 303, 305 includes multiple separate areas 340 in which the areas 340 correspond to respective time periods in which the patient parameter was significant. The areas 340 have at least one of the plurality of potential reference colors. The areas 340 are separated by areas 342, which are insignificant. The insignificant areas 342 have a background color.

As shown in FIGS. 6 and 7, only a portion of the background for each designated time in which the patient parameter is significant has the reference color. For example, at time $t_3$, the patient parameter for the graph region 305 is significant. As such, a vertical column 370 of the background 312 for the designated time $t_3$ has a reference color. However, the reference color is provided for only a portion of the vertical column 370. More specifically, the reference color exists between the parameter signal line 314 and a reference border 372 of the graph region 303. The parameter signal line 314 is a border of the background 312 that has the reference color. In FIG. 7, a visible line (e.g., dashed or solid line) is not shown for the reference border 372. Instead, the reference border 372 extends parallel to a horizontal axis 392 of the health-monitoring window 300 at a designated value of the patient parameter. The designated value of the patient parameter may be established by the system or by user inputs. For example, the reference border 372 may coincide with a lower limit for the patient parameter associated with the graph region 305. In other embodiments, a visible line may define the reference border 372.

Figure 15:
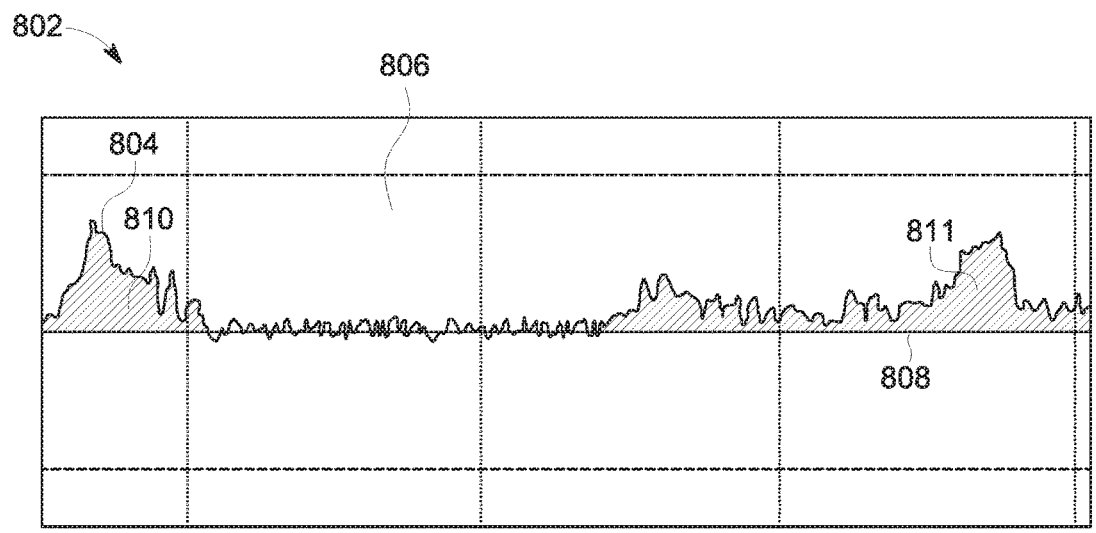
FIG. 15 illustrates a graph region that may be presented to a user in a health-monitoring window in accordance with an embodiment.

FIG. 15 illustrates another example of a graph region 802 that is similar to the graph regions 303, 305 (FIGS. 6 and 7, respectively). The graph region 802 has a signal line 804 that appears over a background 806. The graph region 802 also includes a baseline 808 that extends horizontally across the graph region 802 over the background 806. In the embodiment of FIG. 15, the baseline 808 has a parameter value of 0 and also defines a reference border. For parameter values that are determined to be significant, a reference color is applied to the background between the baseline 808 (or the reference border 808) and the signal line 804. The graph region 802 includes two separate areas 810, 811 having the reference color applied over the background 806.

Figure 8:
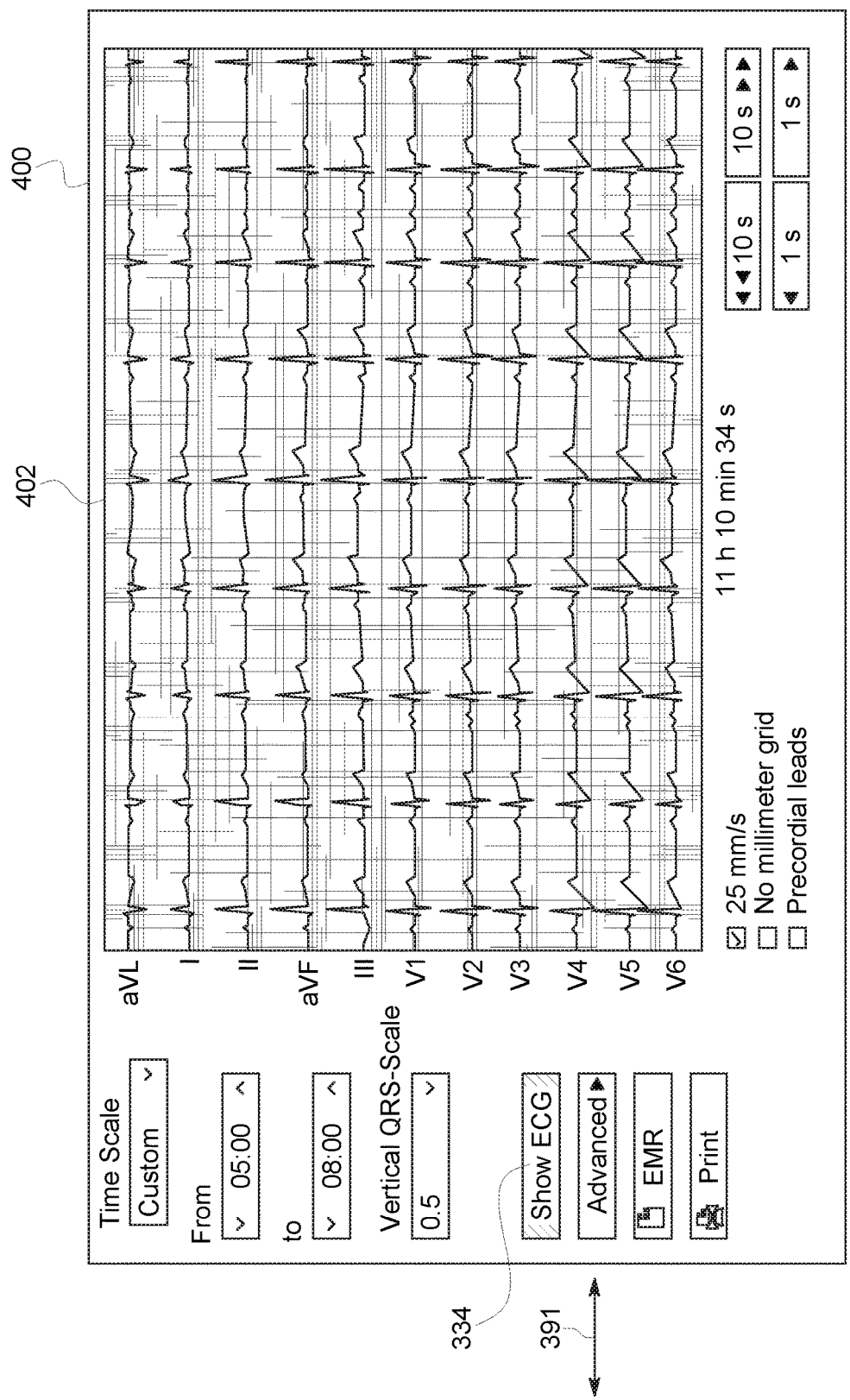
FIG. 8 illustrates a health-monitoring window that may be presented to a user of the system of FIG. 1 in accordance with an embodiment.

FIG. 8 illustrates a health-monitoring window 400 that may be presented to a user of the system in accordance with an embodiment. The health-monitoring window 400 may appear, for example, when the user of the system selects a user-selectable element 334 in the health-monitoring window 400. In FIG. 8, the user-selectable element 334 is labeled "Show ECG." When user inputs select the user-selectable element 334, an electrocardiogram (or ECG) 402 is presented to the user of the system. The ECG may correspond to the location of a time indicator 324 (shown in FIGS. 5 and 9). Optionally, the ECG 402 may have a physical appearance that is identical to conventional paper ECGs.

Figure 9:
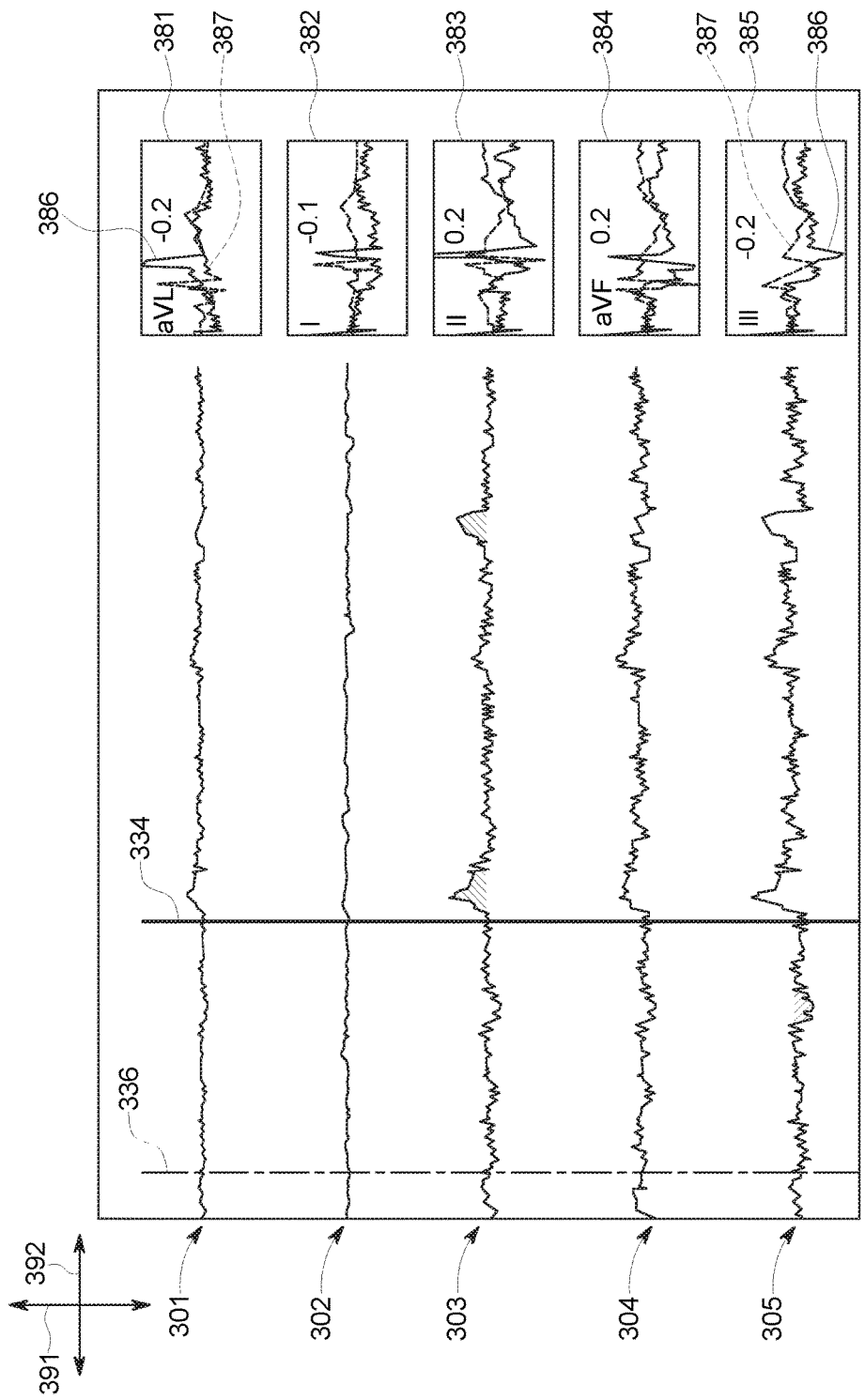
FIG. 9 illustrates a health-monitoring window that may be presented to a user of the system of FIG. 1 in accordance with an embodiment.
Figure 10:
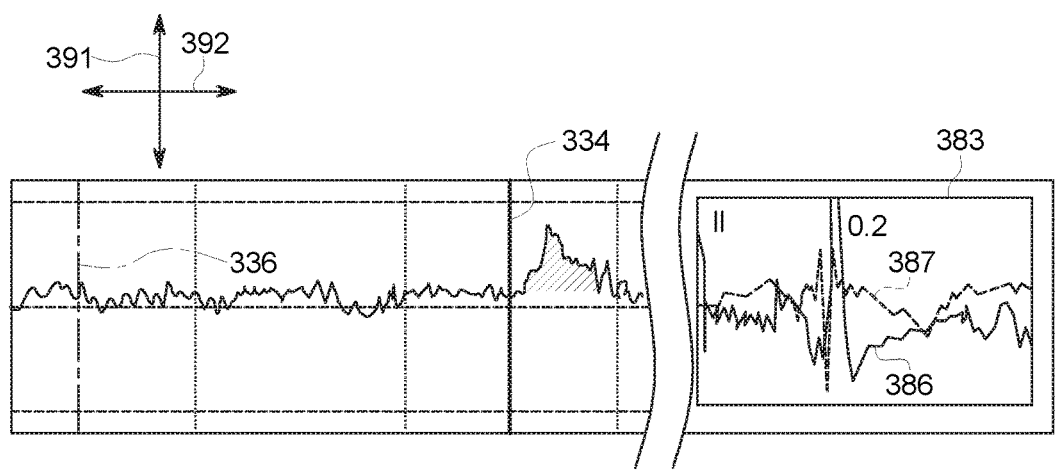
FIG. 10 illustrates a graph region having a graph sub-region of the health-monitoring window of FIG. 9 that may be presented to a user of the system of FIG. 1.

FIG. 9 illustrates only a portion of the health-monitoring window 300, and FIG. 10 illustrates the graph region 303 in greater detail. The time indicator 334 and the graph regions 301-305 are shown in FIG. 9. The time indicator 334 extends generally parallel to a vertical axis 391 of the health-monitoring window 300 and across the graph regions 301-305. The graph regions 301-305 are vertically stacked and synchronized. The time indicator 334 is movable along the horizontal axis 392 of the health-monitoring window 300. In some embodiments, a system is configured to receive user inputs for positioning the time indicator 334 along the horizontal axis 392.

Also shown, the graph regions 301-305 of the health-monitoring window 300 include graph sub-regions 381-385, respectively. The graph sub-regions 381-385 include local signal lines 386, 387. The local signal lines 386 are enlarged portions of the corresponding parameter signal lines 314 of the graph regions 301-305 where the time indicator 334 intersects the corresponding parameter signal lines 314. The local signal lines 387 are enlarged portions of the corresponding parameter signal lines 314 of the graph regions 301-305 where a time indicator 336 intersects the corresponding parameter signal lines 314. The time indicator 336 is shown in FIGS. 9 and 10. Similar to the time indicator 334, the time indicator 336 extends generally parallel to the vertical axis 391 of the health-monitoring window 300 and across the graph regions 301-305. The time indicator 336 is movable along the horizontal axis 392 of the health-monitoring window 300. The system may be configured to receive user inputs for positioning the time indicator 336 along the horizontal axis 392.

Accordingly, each of the graph sub-regions 381-385 includes two local signal lines 386, 387 that correspond to two different times of the monitoring session. For embodiments that enable a user to position the two different time indicators 334, 336 and present the graph sub-regions 381-385, a user of the system may be able to compare the parameter signal lines 314 at different local times or, more specifically, the parameter signal line at the local time identified by the time indicator 334 and the parameter signal line at the local time identified by the time indicator 336. For example, the local time and the parameter signal line associated with each of the graph sub-regions 381-385 corresponds to a single heart beat. In other embodiments, the local time may be a predetermined amount of time (such as, two to five (2-5) seconds), although other values for local times may be selected.

Figure 11:
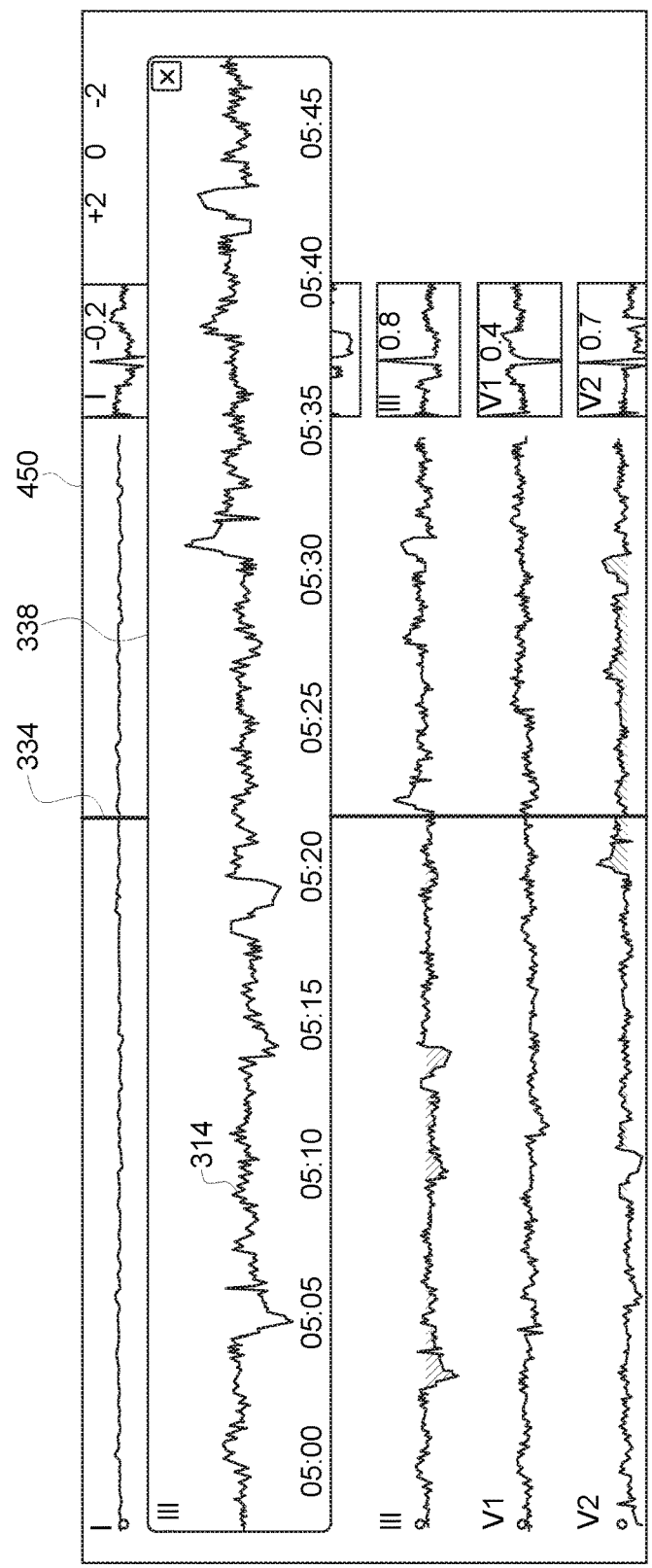
FIG. 11 illustrates a health-monitoring window that may be presented to a user of the system of FIG. 1 in accordance with an embodiment.

FIG. 11 illustrates a portion of the health-monitoring window 450 that may be presented to a user of the system in accordance with an embodiment. The health-monitoring window 450 is identical to the health-monitoring window 300 (FIG. 5), except the health-monitoring window 450 also includes an enlarged segment 338 of the graph region 305. The enlarged segment 338 may appear when a user selects one of the patient parameters. Unlike the sub-regions 381-385 (FIG. 9), the enlarged segment 338 corresponds to a greater time period, such as about one hour. Again, other time periods may be selected to be shown in the enlarged segment 338. The portion of the parameter signal line 314 shown in the enlarged segment 338 is based on a location of the time indicator 334.

Figure 12:
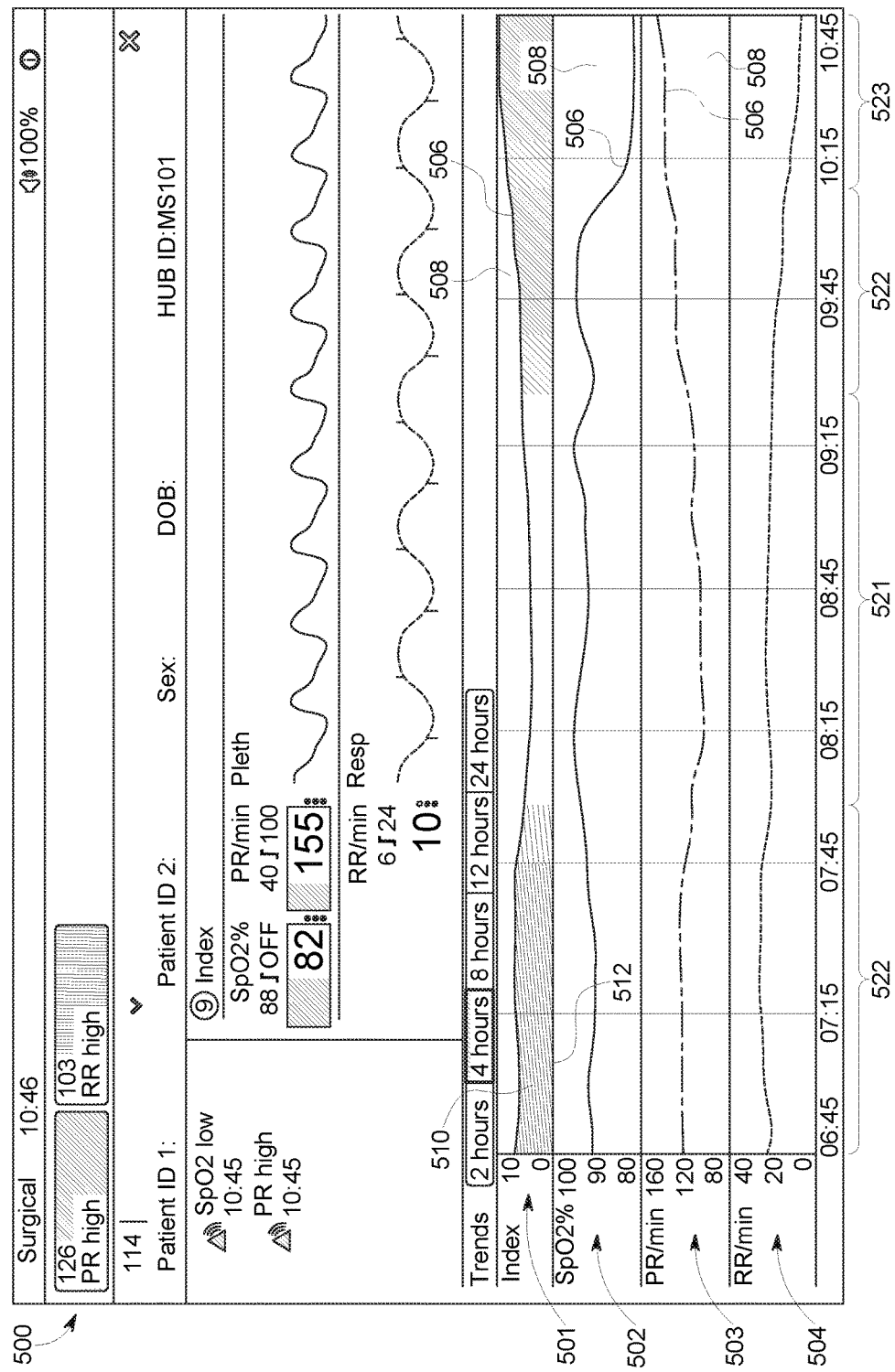
FIG. 12 illustrates a health-monitoring window that may be presented to a user of the system of FIG. 1 in accordance with an embodiment.

FIG. 12 illustrates a health-monitoring window 500 that may be presented to a user of a system in accordance with an embodiment. Similar to the other health-monitoring windows described herein, the health-monitoring window 500 is configured to show a plurality of graph regions 501-505 that each include a parameter signal line 506 associated with a patient parameter and a background 508 that appears behind the parameter signal line 506. At least one of the graph regions 501-505 is similar to other graph regions described herein and is capable of having different areas with different reference colors. More specifically, the graph region 501 represents a patient parameter that is based on a plurality of different patient parameters. More specifically, the parameter signal line 506 of the graph region 501 represents a health index of a patient. The health index is based on the patient parameters that correspond to the graph regions 502-505.

As shown, the graph region 501 includes a parameter field 510 that extends continuously across the graph region 501. The parameter field 510 appears to be over the background 508 and extends vertically between the parameter signal line 506 and a horizontal line 512 of the graph region 501. The background has two different colors, black and white, separated by the parameter signal line 506. The horizontal line 512 may define a border of the graph region 501. The parameter field 510 includes significant areas 522 and 523 in which the different significant areas have different reference colors.

The reference colors may be selected from a plurality of potential reference colors. In the embodiment of FIG. 12, the number of potential reference colors is numerous (e.g., 100 potential reference colors) such that the reference color of the parameter field 510 appears to change seamlessly within a color spectrum. More specifically, in the illustrated embodiment, a vertical line that separates the different areas 522, 523 is not visually identifiable. Nonetheless, FIG. 12 generally indicates the areas 522, 523 in which each area has a unique reference color. In some embodiments, the portion of the area 521 of the background 508 that is below the parameter signal line 506 is white, the portion of the area 521 of the background 508 that is above the parameter signal line 506 is black, the areas 522 are yellow, and the area 523 is red.

If the patient is not in distress, the patient parameter associated with the graph region 501 has a low value and a color that indicates the patient parameter is not significant. If the patient is in distress, the patient parameter associated with the graph region 501 has a high value a reference color that indicates the patient parameter is significant. A color of the background 508 between the parameter signal line 506 and the horizontal line 512 is determined by the value of the patient parameter.

Figure 13:
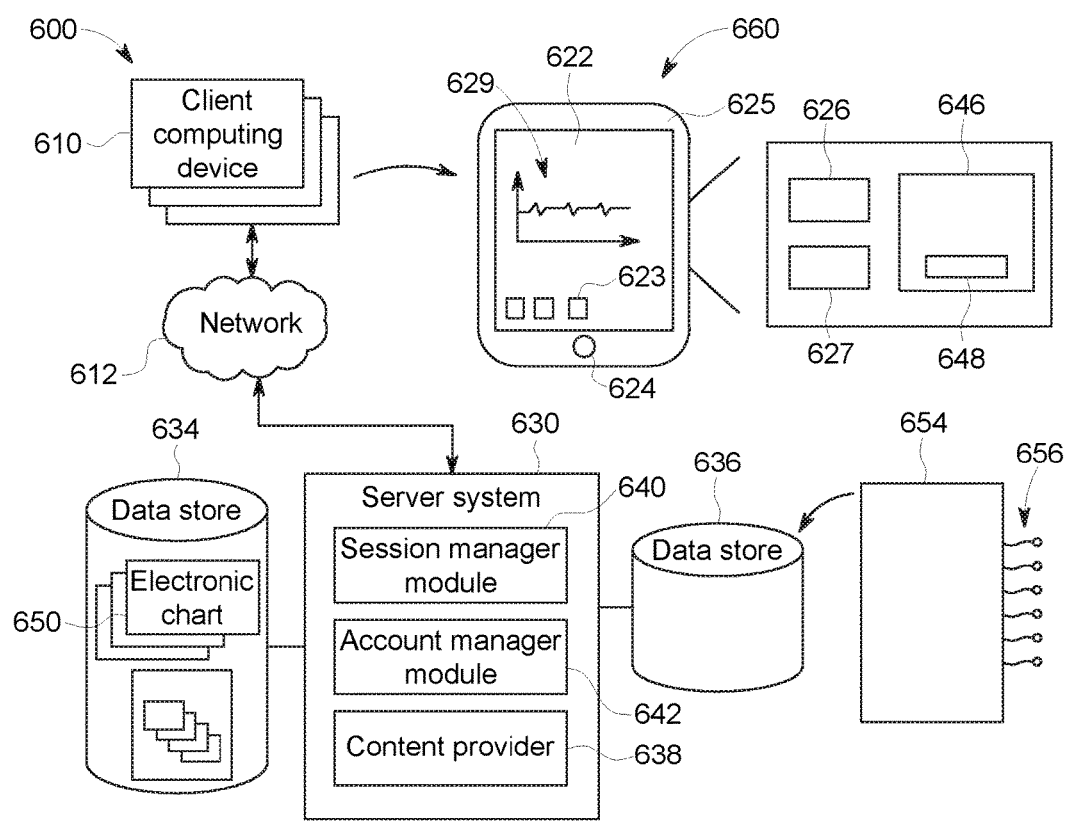
FIG. 13 is a block diagram of an exemplary system in accordance with an embodiment.

FIG. 13 is a block diagram of an exemplary system in accordance with an embodiment. The system 600 includes one or more client computing devices 610 that are capable of communicating over a network 612 with a server system 630. The client computing devices 610 are configured to present one or more of the health-monitoring windows described herein. The server system 630 may include one or more web servers and, optionally, one or more application servers. The server system 630 may host a web application and have the tools, application program interfaces (APIs), and scripts, among other things, that may be used for the web application. In some embodiments, a web application includes a web site or web page that allows a user to view data or information relating to a patient. The server system 630 may be only a single server or include a plurality of different servers that communicate with one another and the client computing devices 610 over the network 612. The server system 630, in some embodiments, is configured to receive and interpret requests through the network 612 from the client computing devices 610 or, more specifically, from software applications 146 of the client computing devices 610. The server system 630 is also configured to respond to the requests and transmit data to the client computing devices 610 in a predetermined format (e.g., HTML format). In some cases, the server system 630 and the client computing devices 610 may form a cloud-type computing system (e.g., public cloud, private cloud, or hybrid cloud).

The network 612 represents any one or combination of multiple different types of networks, such as cable networks, the Internet, private intranets, local area networks, wide area networks, wireless networks, and the like. In particular embodiments, the network 612 is the network of a healthcare facility (e.g., hospital) that allows access to authorized users (e.g., doctors, nurses, technicians, and the like) for reviewing medical information.

The client computing devices 610 may be implemented as any number of types of computing devices. These devices may include, for instance, personal computers (PCs), tablet computers, notebook computers, laptop computers, smart phones, electronic book readers, and so forth. In particular embodiments, the client computing devices 610 may include portable or handheld devices, such as tablet computers, notebook computers, laptop computers, and smart phones (e.g., iPhones). A portable or handheld device is relatively lightweight (e.g., less than six pounds) such that an average adult individual may hold and re-orient the device during the course of its intended operation. In the illustrated embodiment, the computing device is a tablet computer 660. A user may be able to orient the portable device in a first layout orientation (e.g., portrait or vertical orientation) and in a second layout orientation (e.g., landscape or horizontal orientation). Data displayed on the portable devices may include, among other things, data that includes one or more signal lines as set forth herein. The data may be reconfigured (e.g., re-sized) after the orientation of the portable device has changed. In some embodiments, the computing devices may be used for personal use and for business purposes.

The portable devices may also be configured to operate application programs, such as web browsers, mobile applications, or other software programs, that are capable of retrieving the data and displaying the data through a communication network. The application program may be, for example, a third-party program (e.g., Google Chrome), a third-party mobile application (which may or may not include the same functionalities as a conventional web browser), or an application program configured for the enterprise using the application program. For instance, the application program may be developed using WebView. The communication network may include a private network, public network, or both. Non-limiting examples of web browsers include, such as Microsoft's Internet Explorer, Google Chrome, Mozilla Firefox, Opera, and Apple's Safari. The application programs may also be similar to mobile applications (referred to as "apps"). Optionally, the application programs may be configured to work with sub-applications or scripts (e.g., plug-ins or extensions) that are executed from within the application program or in concert with the application program. The sub-application runs or is executed concurrently with the application program. Optionally, the sub-application may be stored within the client computing system and/or the server system.

Application programs are typically third-party software that retrieve, present, and communicate information through the network. Application programs are configured to communicate with the server system 630 over the network 612. The application programs may communicate using, for example, a known protocol (e.g., Hypertext Transfer Protocol (HTTP) or HTTP-secure (HTTPS)). More specifically, the application programs may send requests (e.g., HTTP requests) for information to any web-accessible interne address. The application programs may also display the information in accordance with a predetermined format (e.g., HTML format). The sub-applications may be launched from within the application program and, optionally, communicate with the server system 630 to retrieve information that may be displayed to the user through the application program. Embodiments set forth herein may be implemented, at least in part, using an application program, a sub-application associated with the application program, or other software program having computer executable code.

In some embodiments, the server system 630 is configured to present a site (e.g., a website) that is capable of handling requests from one or more users and transmitting, in response, various pages (e.g., web pages) that are rendered at the client computing devices 610. For instance, the site can be any type of site that allows a user to view the data and, optionally, supports user interaction. In another example, the server system 630 may provide applications or sub-applications for the client computing devices 610 to download, store, and run locally. The server system 630 may additionally or alternatively interact with the client computing devices 610 to provide content in other ways.

As one example, the server system 630 may present an institutional website that allows access to medical data for a user that is authorized to view the medical data. The server system 630 may include, among other things, a content provider module 638, a session manager module 640, and an account manager module 642. The modules 638, 640 and 642, as well as other modules or services described herein, may be implemented by one or more processors performing program instructions to perform the operations described herein. The program instructions may be stored in data stores 634 or 636. The server system 630 interacts with one or more memories or data stores 634 and 636 in various manners as explained herein. One or both of the memories or data stores 634 and 636 may store program instructions to direct one or more processors to carry out the instructions described herein.

The data stores 634, 636 (as well as memory at the client computing devices 610) may also store various information, such as account-specific information about users of the site. The data store 634 may also store one or more catalogs related to items that may be viewed by the user. For example, web content (text, videos, pictures, and other content) may be stored therein. Content may also include electronic chart files 650 (e.g., health-monitoring windows) having graph regions with signal lines as described below. The data associated with different web content may be transmitted to client computing devices 610 in response to individual client request designating location of such web content. It is recognized that the various content may be stored at locations distributed between various data storage areas, geographic locations, file structures, recommendation services, e-commerce catalogs and the like.

During operation, the session manager module 640 maintains network sessions with various client computing devices 610. The session manager module 640 responds to requests from the client computing devices 610 by providing authenticated and unauthenticated network resources. The session manager module 640 reviews incoming requests and determines whether the incoming requests seek access to authenticated or unauthenticated network resources. Requests for an authenticated network resource involve (e.g., require) privilege authentication before the session manager module 640 responds by granting access to the authenticated network resource. When privilege authentication is warranted/needed, the account manager module 642, returns an account lookup response including a prompt for non-sign-in credentials. The non-sign-in credentials corresponding to a type of content maintained in connection with user accounts. The non-sign-in credentials represent user specific information that is unique to a user and is not used as sign-in credentials for a corresponding network service. Optionally, the account manager module 642 may return an account authentication page including at least one of i) a sign-in credential fields or ii) a create new account option. Based on the user's entries at the account authentication page (as explained herein), the account manager module 642 the presents an account lookup response (e.g., when incorrect sign-in credentials are entered). The account manager module 642 may authorize the user to view the medical data, such as the data described herein.

Also shown in FIG. 13, the tablet computer 660 includes an operator display 622, which may be a touchscreen in some embodiments that is configured to identify and locate a touch from a user's finger or stylus. The operator display 622 is framed by a housing 625 of the table computer 660. The operator display 622 defines an area that may present virtual user-selectable elements 623 that may be selected by the user on the operator display 622. Alternatively or in addition to the user-selectable elements 623, a user may select tangible or physical user-selectable elements 624 (e.g., buttons, switches, and the like).

Also shown in FIG. 13, the tablet computer 660 may include one or more processors 626 and computer-readable storage media 627. The computer-readable storage media 627 may store program instructions or computer code for a display application 646. The display application 646 is configured to display an electronic chart 629 on the operator display 622. In some embodiments, the display application 646 is configured to analyze a health-monitoring graph to determine whether the chart is sufficiently displayed (e.g., correct aspect ratio) to the user. In some embodiments, the computer-readable storage media 627 may store program instructions or computer code for a sub-application 648.

Optionally, the sub-application 648 may be a plug-in or extension that is executable within or by the display application 646.

In some embodiments, the system 600 may include a monitoring system (or base unit) 654 that is communicatively coupled to detection devices 656 that are configured to detect measurements, such as from an individual (e.g., a patient), and communicate the measurements to the system 654 as physiological data. In particular embodiments, the measurements are physiological measurements. The detection devices 656 may be configured to detect different physiological measurements, such as a heart rate, body temperature, blood pressure, respiratory rate, electrical activity, or intrauterine pressure. The monitoring system 654 may communicate data to the server system 630 that is based on the detected physiological measurements. For example, the data may include the chart documents described herein and/or may include data for forming the chart documents.

Figure 14:
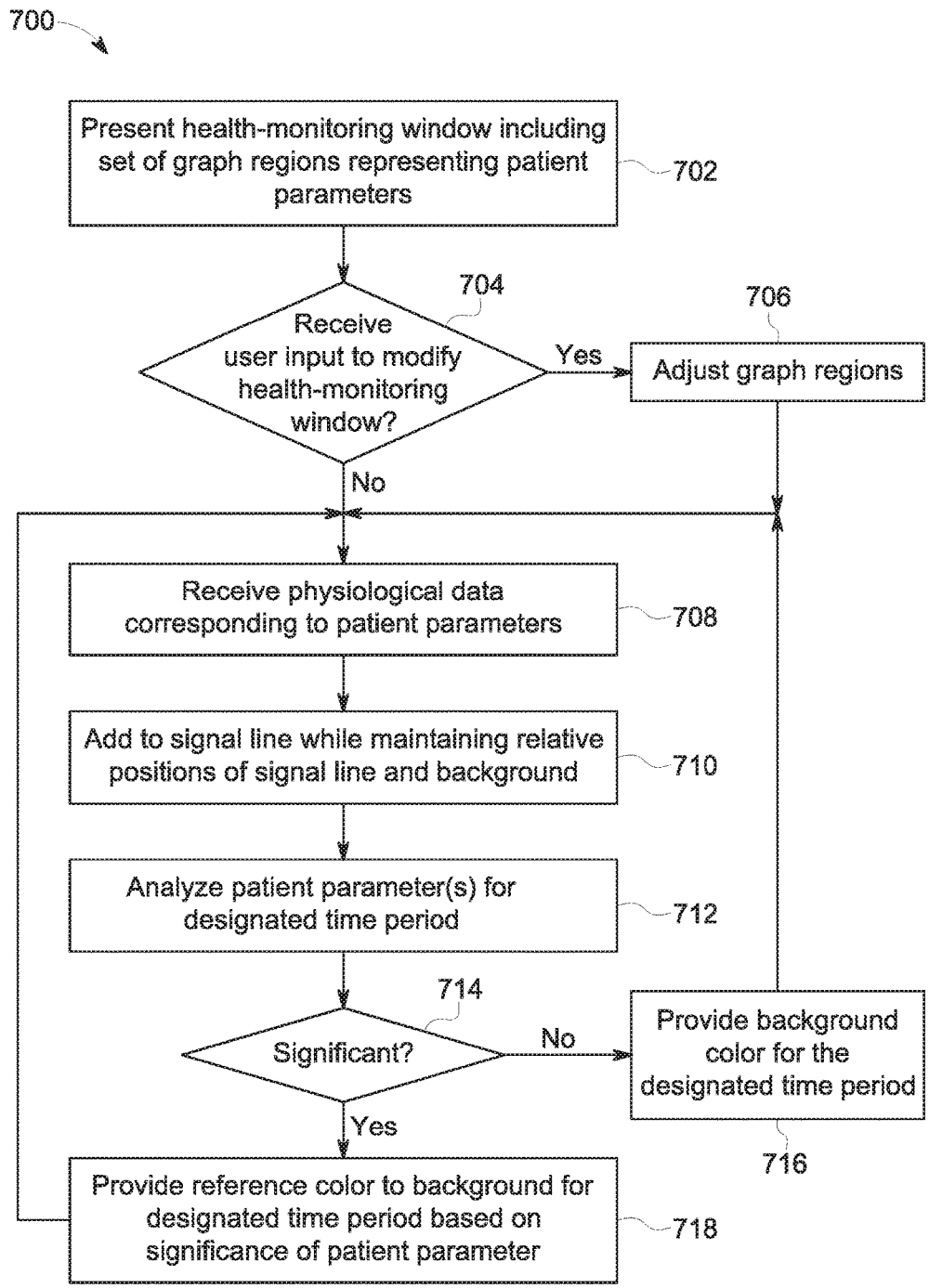
FIG. 14 is a block diagram illustrating a method in accordance with an embodiment.

FIG. 14 illustrates a method 700 in accordance with an embodiment. The method 700 may be performed, at least in part, by embodiments set forth herein. For example, the systems 100 and 600 may be used to perform the method 700. Although the flow chart in FIG. 14 illustrates individual operations, it should be understood that the operations are not necessarily executed at separate times or in the order shown. The method 700 may include presenting, at 702, a health-monitoring window that includes a set of graph regions. Each of the graph regions may include a background with one or more signal lines. The signal lines may represent values of a patient parameter. At 704, a user may provide user inputs for modifying the health-monitoring window. For example, the user may adjust the positions of the graph regions relative to one another. The user may also select a time frame for how long the patient parameters will be shown in the health-monitoring window. The user may also provide the predetermined standards that will be used to determine whether the patient parameters for a designated time period are significant. At 706, the graph regions may be adjusted based on the user inputs. At 704 and 706, other options may be selected and adjusted, respectively, within the health-monitoring window, such as whether to show data for heart rate, movements, and signal quality.

At 708, the physiological data is received. The physiological data may be received directly from detection devices. For example, a base unit may receive the physiological data from the detection devices. Alternatively, the physiological data may be received, at 708, from a server system that is communicatively coupled to a base unit or from a database where the physiological data was stored. In this instance, a healthcare provider may log onto a network using a computing system (e.g., desktop computer or portable communication device). The healthcare provider may then request a multi-parameter record of a patient. Responsive to this request, the server system may communicate the multi-parameter record to the computing system of the healthcare provider. For example, the health-monitoring window may be presented to the healthcare provider and the physiological data may be analyzed to display the patient parameters within the health-monitoring window.

For embodiments used during real-time monitoring, the method 700 includes adding, at 710, new data to the signal line for each graph region while maintaining relative positions of the signal line to the background of the graph region. In such embodiments, the graph regions appear similar to conventional tracing records in which the signal lines move to the left as time progresses and change based on the current physiological data received from the patient.

At 712, the patient parameters for a designated time period are analyzed to determine if the patient parameters (e.g., the values of the patient parameters for the designated time period) are significant. At 714, the method queries whether the patient parameters for the designated time period are significant. If a patient parameter is not significant, at 716, a background color (also called standard color) is provided to the portion of the background for the designated time period. The background color may be a single color (e.g., white). Alternatively, the background color may include a single color below the signal line (e.g., white) and a different color above the signal line (e.g., black). If a patient parameter is significant for the designated time period, then a reference color is provided, at 718, to the background for the designated time period. Optionally, the reference color may be based on the level or degree of significance of the patient parameter for the designated time period. For example, if the patient parameter is proximate to an expected value, the reference color may be lighter or have a greater transparency. If the patient parameter differs from the expected value by a larger amount, the reference color may be more visibly distinct with respect to the background color.

For real-time monitoring applications, as new data is received, the signal lines and the background appear to shift with time. As an example, if the graph region incrementally adds new data for each half-second, the area of the background may have a width associated with a half-second. The actual width along the operator display is based on the size of the operator display, the size of the health-monitoring window within the operator display, and the time frame of the graph region. The height of the background added to the graph region correlates to the height of the graph region. If the patient parameter is significant for the new data that is added, the reference color may be applied to the background. For example, the reference color may be applied to a portion of the area (e.g., the portion between the signal line and another border as shown in FIGS. 6 and 7) or to the entire area (as shown in FIG. 4). If the patient parameter is not significant for the new data that is added, the background color may be applied to the background.

The method 700 may repeat steps 708, 710, 712, and 714 while the patient is being monitored. More specifically, new data points (or new values) may be added to the signal lines of the different patient parameters as time progresses. As each new data point is added, the signal line shifts along the horizontal axis (or time axis) and the background color for each designated time period moves with the signal line.

In some embodiments, the user may enter user inputs as the new data points are added. For example, the user may modify the health-monitoring window as described above with respect to operations 704, 706. If the health-monitoring window is adjusted in a manner that affects the display of the graph regions, then embodiments may not only adjust the graph regions for new data points but also the graph regions for past data points. For example, if a user adjusts the predetermined standards by which the patient parameters are analyzed to determine significance, embodiments may analyze past data using the adjusted standards to determine if the significance of the past data points has changed. As such, the significance of past data points may change and the color associated with the designated time periods for the past data points may change. As an example, the background for a designated time period may change from the background color to a reference color. One reference color may change to a darker reference color. Alternatively, the background for a designated time period may change from a reference color to the background color.

Accordingly, embodiments may display one or more patient parameters over an extended period of time and visually indicate when, and for how long, the patient parameters were significant. Moreover, embodiments may simultaneously display the type of significance (e.g., too high, too low, etc.) and a degree of significance. By enabling the healthcare provider to view the history of a patient parameter, including the time periods in which the patient parameter was significant and insignificant, the healthcare provider may be able to more quickly identify a pattern for assessing the health status of the patient. For example, the pattern may include one or more areas that visually indicate when a patient parameter was too high or too low and/or one or more areas that visually indicate when a patient parameter is within a designated range or not within a designated range. Moreover, the pattern shows the duration of the significant and insignificant time periods. For embodiments that display multiple parameters, the healthcare provider may view these significant time periods and insignificant time periods for multiple parameters over the extended time period.

It is noted that the patterns are not required to be established or known patterns for the type of patient monitoring being implemented. The patterns may only be those patterns recognized by the healthcare provider using his or her experience with the type of patient monitoring being used. Embodiments may enable the healthcare provider to more easily recognize a pattern by permitting the healthcare provider to at least one of: (a) select the graph regions to display (or the patient parameters to display); (b) select the relative positions of the graph regions (or select the arrangement of the graph regions); (c) select the predetermined standards used to determine whether a patient parameter is significant; or (d) select a scale used by the graph regions.

Although not shown in FIG. 14, the method 700 may also include receiving user inputs for other operations. For example, the user inputs may include requests to view another window (e.g., view ECG record), move time indicators to compare different signal lines, enlarge or minimize sub-windows, enlarge or minimize one or more graph regions or other parts of the health-monitoring window.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
an operator display;
a processor and a storage medium that is configured to store programmed instructions accessible by the processor, wherein, responsive to execution of the programmed instructions, the processor is configured to present a health-monitoring window in the operator display, the health-monitoring window being based on physiological data of a patient and including a set of graph regions, each of the graph regions of the set having a background and a signal line of a patient parameter appearing over the background, the signal line being plotted with respect to horizontal and vertical axes of the health-monitoring window, the horizontal axis representing time and the vertical axis representing the patient parameter of the signal line that is based on the physiological data;
wherein, for at least one of the graph regions of the set, the processor is also configured to:
determine that the patient parameter for a designated time is significant based upon a predetermined standard; and
provide, in response to determining that the patient parameter is significant for the designated time, one or more of a reference color or a reference hatching to the background for the designated time, the reference color including at least one of a plurality of potential reference colors, the background or the designated time having a fixed position with respect to the parameter signal line such that an area of the background having the reference color appears to move along the horizontal axis with the parameter signal line as time progresses, wherein the reference color is selected from the potential reference colors based on a significance of the patient parameter and based on whether the patient parameter is above an upper limit or below a lower limit, the reference color above the upper limit and the reference color below the lower limit have respective wavelengths, the wavelengths being separated by at least 30 nanometers (nm).

2. The system of claim 1, wherein the processor is configured to display multiple separate areas of the background in which the separate areas correspond to respective time periods in which the patient parameter was significant, the separate areas having at least one of the plurality of potential colors.

3. The system of claim 1, wherein the background has a background color for time periods in which the patient parameter is not significant, the background color being distinct with respect to the potential reference colors.

4. The system of claim 1, wherein the processor is configured to determine that the patient parameter of the corresponding graph region is significant for at least a plurality of the graph regions, wherein for each of the graph regions of the plurality, the processor assigns a corresponding reference color to the background for a designated time in response to determining that the patient parameter is significant for the designated time, the reference color including at least one of a plurality of potential reference colors, the background for the designated time having a fixed position with respect to the parameter signal line such that an area of the background having the reference color moves along the horizontal axis with the parameter signal line as time progresses.

5. The system of claim 4, wherein at least some of the graph regions of the plurality of the graph regions are vertically stacked and the parameter signal lines of the graph regions that are vertically stacked are essentially synchronized, the health-monitoring window including a time indicator that extends generally parallel to, the vertical axis of the health-monitoring window and across the graph regions that are vertically stacked, the time indicator being movable along the horizontal axis of the health-monitoring window, the processor configured to receive user inputs for positioning the time indicator along the horizontal axis.

6. The system of claim 1, wherein the health-monitoring window is configured to include a color legend, the color legend including the potential reference colors for viewing, by a user of the system, the color legend also including a scale that associates values with the potential reference colors.

7. The system of claim 1, wherein the patient parameters correspond to electrocardiographic (ECG) data.

8. The system of claim 1, wherein the processor is configured to change the reference color based on the significance of the patient parameter.

9. The system of claim 1, wherein only a portion of the background for the designated time has the reference color, the reference color existing between the parameter signal line and a horizontal line of the graph region, the parameter signal line being a border of the background that has the reference color.

10. The system of claim 1, wherein the reference color extends between a top horizontal line positioned above the parameter signal line and a bottom horizontal line positioned below the parameter signal line, the parameter signal line being visible over the background that has the reference color.

11. The system of claim 1, wherein the processor is configured to receive user inputs for selecting at least one of the, upper limit of the lower limit.

12. A method for monitoring a condition of a patient, the method comprising:
receiving physiological data from a patient;
presenting a health-monitoring window in an operator display, the health-monitoring window including a set of graph regions, each of the graph regions of the set having a background and a parameter signal line appearing over the background, the parameter signal line being plotted with respect to horizontal and vertical axes of the health-monitoring window, the horizontal axis representing time and the vertical axis representing a patient parameter that is based on the physiological data;
wherein, for at least sonic of the graph regions, the method also includes:
determining that the patient parameter of a corresponding graph region is significant for a designated time;
providing one or more of a reference color or a reference hatching to the background of the corresponding graph region for the designated time, the reference color including at least one of a plurality of potential reference colors, the background for the designated time having a fixed position with respect to the parameter signal line such that an area of the background having the reference color moves along the horizontal axis with the parameter signal line as time progresses, wherein the reference color is selected from the potential reference colors based on whether the patient parameter is above an upper limit or below a lower limit, the reference color above the upper limit and the reference color below the lower limit have respective wavelengths, the wavelengths being separated by at least 30 nanometers (nm), wherein the reference color is configured to change based on the significance of the patient parameter.

13. The method of claim 12, wherein the background is configured to include multiple separate areas in which the separate areas correspond to respective time periods in which the patient parameter was significant, the separate areas having at least one of the plurality of potential colors.

14. The method of claim 12, wherein the background has a background color for time periods in which the patient parameter is not significant, the background color being distinct with respect to the potential reference colors.

15. The method of claim 12, further comprising receiving user inputs fir selecting at least one of the upper limit or the lower limit.

16. The method of claim 12, wherein at least some of the graph regions of the plurality of the graph regions are vertically stacked and the parameter signal lines of the graph regions that are vertically stacked are essentially synchronized, the health-monitoring window including a time indicator that extends generally parallel to the vertical axis of the health-monitoring window and across the graph regions that are vertically stacked, the time indicator being movable along the horizontal axis of the health-monitoring window, wherein the method further comprises receiving user inputs for positioning the time indicator along the horizontal axis.

17. The method of claim 12, wherein the health-monitoring window is configured to include a color legend, the color legend including the potential reference colors for viewing by a user of the system, the color legend also including a scale that associates values with the potential reference colors.

18. A monitoring: system configured to monitor a condition of a patient comprising;
an operator display;
a base unit configured to communicatively couple to a plurality of detection devices that detect physiological data of a patient;
a processor and a storage medium that is configured to store programmed instructions accessible by the processor, wherein, responsive to execution of the programmed instructions, the processor is configured to receive the physiological data from the detection devices and present a health-monitoring window in the operator display, the health-monitoring, window being based on the physiological data and including a set of graph regions, each of the graph regions of the set having a background and a parameter signal line appearing over the background, the parameter signal line being plotted with respect to horizontal and vertical axes of the health-monitoring window, the horizontal axis representing time and the vertical axis representing a patient parameter that is based on the physiological data, the parameter signal line appearing to move along the horizontal axis as time progresses;

wherein, for each of the graph regions of the set, the processor performs the following operations when executing the programmed instructions:

monitors the patient parameter associated with the corresponding graph region as the time progresses, the parameter signal line changing as the patient parameter changes;

determines that the patient parameter of the corresponding graph region for a designated time is, significant; and automatically provides, in response to determining that the patient parameter is significant for the designated time, a reference color to the background for the designated time, the reference color including at least one of a plurality of potential reference colors, the background for the designated time having a fixed position with respect to the parameter signal line such that an area of the background having the reference color moves along the horizontal axis with the parameter signal line as time progresses, wherein the processor is configured to change the reference color based on the significance of the patient parameter, wherein the reference color is selected from the potential reference colors based on whether the patient parameter is above an upper limit or below a lower limit, the reference color above the upper limit and the reference color below the lower limit have respective wavelengths, the wavelengths being separated by at least 30 nanometers (nm);

wherein the graph regions of the set are positioned relative to one another to form a multi-parameter record of a patient, the respective areas of the graph regions of the set forming a pattern that enables a user of the system to assess a health status of the patient.

19. The monitoring system of claim 18, wherein the graph regions set are vertically stacked and the parameter signal lines of the graph regions are essentially synchronized, the health-monitoring window including a time indicator that extends generally parallel to the vertical axis of the health-monitoring window and across the graph regions, the time indicator being movable along the horizontal axis of the health-monitoring window, the processor configured to receive user inputs for positioning the time indicator along, the horizontal axis.

20. The monitoring system of claim 19, wherein the health-monitoring window includes graph sub-regions that correspond to the graph regions, the graph sub-regions including local signal lines, the local signal lines being enlarged portions of the corresponding parameter signal lines of the graph regions where the time indicator intersects the corresponding parameter signal lines.

\* \* \* \* \*